United States Patent
Piper et al.

(10) Patent No.: US 7,534,426 B2
(45) Date of Patent: May 19, 2009

(54) GLUTENASE ENZYME ASSAYS

(75) Inventors: Justin L. Piper, Chicago, IL (US); Gary M. Gray, Stanford, CA (US); Chaitan Khosla, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 275 days.

(21) Appl. No.: 11/107,539

(22) Filed: Apr. 15, 2005

(65) Prior Publication Data

US 2006/0002917 A1    Jan. 5, 2006

Related U.S. Application Data

(60) Provisional application No. 60/565,684, filed on Apr. 26, 2004.

(51) Int. Cl.
*A61K 38/48*     (2006.01)
*G01N 33/573*    (2006.01)
*C12Q 1/37*      (2006.01)
*A01N 37/18*     (2006.01)

(52) U.S. Cl. .................. 424/94.63; 424/94.64; 435/7.4; 435/24; 514/2

(58) Field of Classification Search ........................ None
See application file for complete search history.

(56) References Cited

U.S. PATENT DOCUMENTS

| | | | |
|---|---|---|---|
| 5,817,523 A * | 10/1998 | Picarelli | ..................... 436/503 |
| 5,834,428 A | 11/1998 | Drucker | |
| 6,197,356 B1 | 3/2001 | Girsh | |
| 6,319,726 B1 | 11/2001 | Schuppan et al. | |
| 6,410,550 B1 | 6/2002 | Coe et al. | |
| 7,144,569 B1 | 12/2006 | Anderson et al. | |
| 2001/0036639 A1 | 11/2001 | Fine | |
| 2004/0241664 A1 | 12/2004 | Dekker et al. | |
| 2005/0244823 A1* | 11/2005 | Drijfhout et al. | ............... 435/6 |
| 2006/0178299 A1 | 8/2006 | Anderson et al. | |

FOREIGN PATENT DOCUMENTS

| | | |
|---|---|---|
| EP | 0 905 518 A1 | 3/1999 |
| WO | WO 94/26774 | 11/1994 |
| WO | 01/25793 | 4/2001 |
| WO | WO 01/25793 A2 | 4/2001 |
| WO | WO 03/068170 A2 | 8/2003 |

OTHER PUBLICATIONS

Shan L et al (2002) Structural basis for gluten intolerance in celiac sprue. Science, vol. 297, pp. 2275-2279.*
de Ritis G et al (1988) In vitro (organ culture) studies of the toxicity of specific A-Gliadin peptides in celiac disease. Gastroenterology, vol. 94, pp. 41-49.*
Vader et al (2002) The gluten response in children with celiac disease is directed toward multiple gliadin and glutenin peptides. Gastroenterology, vol. 122, pp. 1729-1737.*
Ahnen, et al., "Intestinal aminooligopeptidase in vivo synthesis on intracellular membranes of rat jejunum," (1982) *The Journal of Biological Chemistry*, 257:12129-12935.
Arentz-Hansen, et al., "The intestinal T cell response to α-gliadin in adult celiac disease is focused on a single deamidated glutamine targeted by tissue transolutaminase," (2000) *The Journal of Experimental Medicine*, 191:603-612.
Bordusa, et al., "The specificity of prolyl endopeptidase from *Flavobacterium meningoseptum*: mapping the s' subsites by positional scanning via acyl transfer," (1998) *Bioorganic & Medicinal Chemistry*, 6:1775-1780.
Lahteenoja, et al., "Local challenge on oral mucosa with an α-gliadin related synthetic peptide in patients with celiac disease," (2000) *American Journal of Gastroenterology*, 95:2880.
Schuppan and Detlef, "Special reports and reviews: Current concepts of celiac disease pathogenesis," (2000) *Gastroenterology*, 119:234-42.
Wieser, "The precipitating factor in coeliac disease," (1995) *Ballière's Clinical Gastroenterology*, 9(2):191-207.
Yoshimoto, et al., "Prolyl endopeptidase from *Flavobacterium meningosepticum*: cloning and sequencing of the enzyme gene," (1991) *The Journal of Biochemistry*, 110:873-878.
Database Derwent, "HLA-binding oligopeptide and an immunoregulator contgit—used in the treatment of auto-immune disease," (1996)ACC-No. 1996-329479.

* cited by examiner

*Primary Examiner*—Lisa J Hobbs
(74) *Attorney, Agent, or Firm*—Bozicevic, Field & Francis LLP; Pamela J. Sherwood

(57) ABSTRACT

Administering an effective dose of glutenase to a Celiac or dermatitis herpetiformis patient reduces levels of toxic gluten oligopeptides, thereby attenuating or eliminating the damaging effects of gluten.

13 Claims, 5 Drawing Sheets

SEQUENCE LISTING

```
<160> NUMBER OF SEQ ID NOS: 30

<210> SEQ ID NO 1
<211> LENGTH: 12
<212> TYPE: PRT
<213> ORGANISM: Triticum aestivum

<400> SEQUENCE: 1

Gln Leu Gln Pro Phe Pro Gln Pro Gln Leu Pro Tyr
1               5                   10
```

```
<210> SEQ ID NO 2
<211> LENGTH: 6
<212> TYPE: PRT
<213> ORGANISM: Triticum aestivum
<220> FEATURE:
<221> NAME/KEY: VARIANT
<222> LOCATION: (6)...(6)
<223> OTHER INFORMATION: Tyrosine modified with NO2

<400> SEQUENCE: 2

Gln Pro Gln Gln Pro Tyr
 1               5

<210> SEQ ID NO 3
<211> LENGTH: 14
<212> TYPE: PRT
<213> ORGANISM: Triticum aestivum

<400> SEQUENCE: 3

Pro Gln Pro Gln Leu Pro Tyr Pro Gln Pro Gln Leu Pro Tyr
 1               5                  10

<210> SEQ ID NO 4
<211> LENGTH: 26
<212> TYPE: PRT
<213> ORGANISM: Triticum aestivum

<400> SEQUENCE: 4

Phe Leu Gln Pro Gln Gln Pro Phe Pro Gln Gln Pro Gln Gln Pro Tyr
 1               5                  10                  15

Pro Gln Gln Pro Gln Gln Pro Phe Pro Gln
            20                  25

<210> SEQ ID NO 5
<211> LENGTH: 9
<212> TYPE: PRT
<213> ORGANISM: Triticum aestivum

<400> SEQUENCE: 5

Ile Gln Pro Gln Gln Pro Ala Gln Leu
 1               5

<210> SEQ ID NO 6
<211> LENGTH: 11
<212> TYPE: PRT
<213> ORGANISM: Triticum aestivum

<400> SEQUENCE: 6

Lys Gly His His Glu Ala Glu Leu Lys Pro Leu
 1               5                  10

<210> SEQ ID NO 7
<211> LENGTH: 19
<212> TYPE: PRT
<213> ORGANISM: Triticum aestivum

<400> SEQUENCE: 7

Leu Gly Gln Gln Gln Pro Phe Pro Pro Gln Gln Pro Tyr Pro Gln Pro
 1               5                  10                  15

Gln Pro Phe

<210> SEQ ID NO 8
<211> LENGTH: 6
<212> TYPE: PRT
<213> ORGANISM: Triticum aestivum
```

```
<400> SEQUENCE: 8

Pro Gln Pro Gln Leu Pro
 1               5

<210> SEQ ID NO 9
<211> LENGTH: 16
<212> TYPE: PRT
<213> ORGANISM: Triticum aestivum

<400> SEQUENCE: 9

Leu Gln Leu Gln Pro Phe Pro Gln Pro Gln Leu Pro Tyr Pro Gln Pro
 1               5                  10                  15

<210> SEQ ID NO 10
<211> LENGTH: 9
<212> TYPE: PRT
<213> ORGANISM: Triticum aestivum

<400> SEQUENCE: 10

Pro Phe Ser Gln Gln Gln Gln Pro Val
 1               5

<210> SEQ ID NO 11
<211> LENGTH: 13
<212> TYPE: PRT
<213> ORGANISM: Triticum aestivum

<400> SEQUENCE: 11

Pro Gln Pro Gln Leu Pro Tyr Pro Gln Pro Gln Leu Pro
 1               5                  10

<210> SEQ ID NO 12
<211> LENGTH: 33
<212> TYPE: PRT
<213> ORGANISM: Triticum aestivum

<400> SEQUENCE: 12

Leu Gln Leu Gln Pro Phe Pro Gln Pro Gln Leu Pro Tyr Pro Gln Pro
 1               5                  10                  15

Gln Leu Pro Tyr Pro Gln Pro Gln Leu Pro Tyr Pro Gln Pro Gln Pro
             20                  25                  30

Phe

<210> SEQ ID NO 13
<211> LENGTH: 10
<212> TYPE: PRT
<213> ORGANISM: Triticum aestivum

<400> SEQUENCE: 13

Gln Pro Gln Gln Ser Phe Pro Gln Gln Gln
 1               5                  10

<210> SEQ ID NO 14
<211> LENGTH: 12
<212> TYPE: PRT
<213> ORGANISM: Triticum aestivum

<400> SEQUENCE: 14

Gln Leu Gln Pro Phe Pro Gln Pro Glu Leu Pro Tyr
 1               5                  10
```

```
<210> SEQ ID NO 15
<211> LENGTH: 14
<212> TYPE: PRT
<213> ORGANISM: Triticum aestivum

<400> SEQUENCE: 15

Pro Gln Pro Glu Leu Pro Tyr Pro Gln Pro Glu Leu Pro Tyr
1               5                   10

<210> SEQ ID NO 16
<211> LENGTH: 10
<212> TYPE: PRT
<213> ORGANISM: Triticum aestivum

<400> SEQUENCE: 16

Gln Pro Gln Gln Ser Phe Pro Glu Gln Gln
1               5                   10

<210> SEQ ID NO 17
<211> LENGTH: 13
<212> TYPE: PRT
<213> ORGANISM: Triticum aestivum

<400> SEQUENCE: 17

Pro Gln Pro Glu Leu Pro Tyr Pro Gln Pro Gln Leu Pro
1               5                   10

<210> SEQ ID NO 18
<211> LENGTH: 14
<212> TYPE: PRT
<213> ORGANISM: Triticum aestivum

<400> SEQUENCE: 18

Pro Gln Pro Glu Leu Pro Tyr Pro Gln Pro Gln Pro Leu Pro
1               5                   10

<210> SEQ ID NO 19
<211> LENGTH: 5
<212> TYPE: PRT
<213> ORGANISM: Triticum aestivum
<220> FEATURE:
<221> NAME/KEY: VARIANT
<222> LOCATION: (1)...(1)
<223> OTHER INFORMATION: Z modified Gly

<400> SEQUENCE: 19

Gly Pro Leu Gly Pro
1               5

<210> SEQ ID NO 20
<211> LENGTH: 5
<212> TYPE: PRT
<213> ORGANISM: Triticum aestivum

<400> SEQUENCE: 20

Pro Gln Pro Gln Pro
1               5

<210> SEQ ID NO 21
<211> LENGTH: 14
<212> TYPE: PRT
<213> ORGANISM: Triticum aestivum

<400> SEQUENCE: 21

Pro Gln Gln Pro Gln Gln Ser Phe Pro Gln Gln Gln Arg Pro
1               5                   10
```

-continued

```
<210> SEQ ID NO 22
<211> LENGTH: 32
<212> TYPE: PRT
<213> ORGANISM: Triticum aestivum
<220> FEATURE:
<221> NAME/KEY: PYRROLIDONE CAR
<222> LOCATION: (1)...(1)
<223> OTHER INFORMATION: N terminal pyroglutaminate

<400> SEQUENCE: 22

Gln Leu Gln Pro Phe Pro Gln Pro Gln Leu Pro Tyr Pro Gln Pro Gln
1               5                   10                  15

Leu Pro Tyr Pro Gln Pro Gln Leu Pro Tyr Pro Gln Pro Gln Pro Phe
            20                  25                  30

<210> SEQ ID NO 23
<211> LENGTH: 7
<212> TYPE: PRT
<213> ORGANISM: Triticum aestivum

<400> SEQUENCE: 23

Gln Leu Pro Tyr Pro Gln Pro
1               5

<210> SEQ ID NO 24
<211> LENGTH: 17
<212> TYPE: PRT
<213> ORGANISM: Triticum aestivum

<400> SEQUENCE: 24

Gln Leu Pro Tyr Pro Gln Pro Gln Leu Pro Tyr Pro Gln Pro Gln Pro
1               5                   10                  15

Phe

<210> SEQ ID NO 25
<211> LENGTH: 32
<212> TYPE: PRT
<213> ORGANISM: Triticum aestivum

<400> SEQUENCE: 25

Gln Leu Gln Pro Phe Pro Gln Pro Gln Leu Pro Tyr Pro Gln Pro Gln
1               5                   10                  15

Leu Pro Tyr Pro Gln Pro Gln Leu Pro Tyr Pro Gln Pro Gln Pro Phe
            20                  25                  30

<210> SEQ ID NO 26
<211> LENGTH: 7
<212> TYPE: PRT
<213> ORGANISM: Triticum aestivum

<400> SEQUENCE: 26

Gln Pro Gln Leu Pro Tyr Pro
1               5

<210> SEQ ID NO 27
<211> LENGTH: 9
<212> TYPE: PRT
<213> ORGANISM: Triticum aestivum

<400> SEQUENCE: 27

Gln Gln Pro Gln Gln Pro Tyr Pro Gln
1               5
```

```
<210> SEQ ID NO 28
<211> LENGTH: 9
<212> TYPE: PRT
<213> ORGANISM: Triticum aestivum

<400> SEQUENCE: 28

Ser Gln Pro Gln Gln Gln Phe Pro Gln
1               5

<210> SEQ ID NO 29
<211> LENGTH: 14
<212> TYPE: PRT
<213> ORGANISM: Triticum aestivum

<400> SEQUENCE: 29

Val Ser Phe Gln Gln Pro Gln Gln Gln Tyr Pro Ser Ser Gln
1               5                   10

<210> SEQ ID NO 30
<211> LENGTH: 8
<212> TYPE: PRT
<213> ORGANISM: Triticum aestivum

<400> SEQUENCE: 30

Trp Gln Ile Pro Glu Gln Ser Arg
1               5
```

GLUTENASE ENZYME ASSAYS

This invention was made with Government support under contract DK063158 awarded by the National Institutes of Health. The Government has certain rights in this invention.

BACKGROUND OF THE INVENTION

In 1953, it was first recognized that ingestion of gluten, a common dietary protein present in wheat, barley and rye causes disease in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac Sprue is generally considered to be an autoimmune disease and the antibodies found in the serum of the patients supports a theory of an immunological nature of the disease. Antibodies to tissue transglutaminase (tTG) and gliadin appear in almost 100% of the patients with active Celiac Sprue, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villus atrophy of the small intestine.

At the present time there is no good therapy for the disease, except to completely avoid all foods containing gluten. Although gluten withdrawal has transformed the prognosis for children and substantially improved it for adults, some people still die of the disease, mainly adults who had severe disease at the outset. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac Sprue, improved methods of treating or ameliorating the effects of the disease are needed. The present invention addresses such needs.

SUMMARY OF THE INVENTION

The present invention provides methods for treating the symptoms of Celiac Sprue and/or dermatitis herpetiformis by decreasing the levels of toxic gluten oligopeptides in foodstuffs, either prior to or after ingestion by a patient. By digestion with glutenases, these toxic oligopeptides are cleaved into fragments, thereby preventing or relieving their toxic effects in Celiac Sprue or dermatitis herpetiformis patients.

In one embodiment of the invention, methods are provided for determining the therapeutic efficacy of a candidate glutenase enzyme. Methods of interest include in vitro and in vivo screening of enzymes. Such methods may comprise detecting the ability of a candidate enzyme to digest gliadin peptides, including specific peptides provided herein, and determining the ability of the enzyme to digest the peptides to non-toxic fragments. HPLC is optionally utilized to determine the length of digestions products. For determination of pharmacologically useful dosages, in vivo perfusion assays may be utilized.

In one aspect of the invention, a foodstuff is treated with a glutenase prior to consumption by the patient. In another aspect of the invention, a glutenase is administered to a patient and acts internally to destroy the toxic oligopeptides. In another aspect of the invention, a recombinant organism that produces a glutenase is administered to a patient. In another aspect of the invention, gene therapy is used to provide the patient with a gene that expresses a glutenase that destroys the toxic oligopeptides.

In one aspect, the invention provides methods for the administration of enteric formulations of one or more glutenases, each of which may be present as a single agent or a combination of active agents. In another aspect of the invention, stabilized forms of glutenases are administered to the patient, which stabilized forms are resistant to digestion in the stomach, e.g. to acidic conditions. Alternative methods of administration include genetic modification of patient cells, e.g. enterocytes, to express increased levels of peptidases capable of cleaving immunogenic oligopeptides of gliadin; pretreatment of foods with glutenases; the introduction of micro-organisms expressing such peptidases so as to transiently or permanently colonize the patient intestinal tract; and the like.

In another aspect, the invention provides pharmaceutical formulations containing one or more glutenases and a pharmaceutically acceptable carrier. Such formulations include formulations in which the glutenase is contained within an enteric coating that allows delivery of the active agent to the intestine and formulations in which the active agents are stabilized to resist digestion in acidic stomach conditions. The formulation may comprise one or more glutenases or a mixture or "cocktail" of agents having different activities.

In another aspect, the invention provides foodstuffs derived from gluten-containing foods that have been treated to remove or to reduce to non-toxic levels the gluten-derived oligopeptides that are toxic to Celiac Sprue patients, and methods for treating foods to hydrolyze toxic gluten oligopeptides. In other aspects, the invention provides recombinant microorganisms useful in hydrolyzing the gluten-derived oligopeptides that are toxic to Celiac Sprue patients from foodstuffs; methods for producing glutenases that digest the gluten-derived oligopeptides that are toxic to Celiac Sprue patents; purified preparations of the glutenases that digest the gluten-derived oligopeptides that are toxic to Celiac Sprue patents; and recombinant vectors that code for the expression of glutenases that digest the gluten-derived oligopeptides that are toxic to Celiac Sprue patents.

These and other aspects and embodiments of the invention are described in more detail below.

BRIEF DESCRIPTION OF THE DRAWINGS

FIG. 5B: The concentration profile model was adapted to illustrate the effective proteolysis of 50 µM P5 when supplemented with increasing concentrations of prolyl endopeptidase (PEP). A) 0.0, B) 25 µU/µL, C)125 µU/µL, D) 155 µU/µL and E) 190 µU/µL recombinant PEP.

DETAILED DESCRIPTION OF THE EMBODIMENTS

Figure 1:
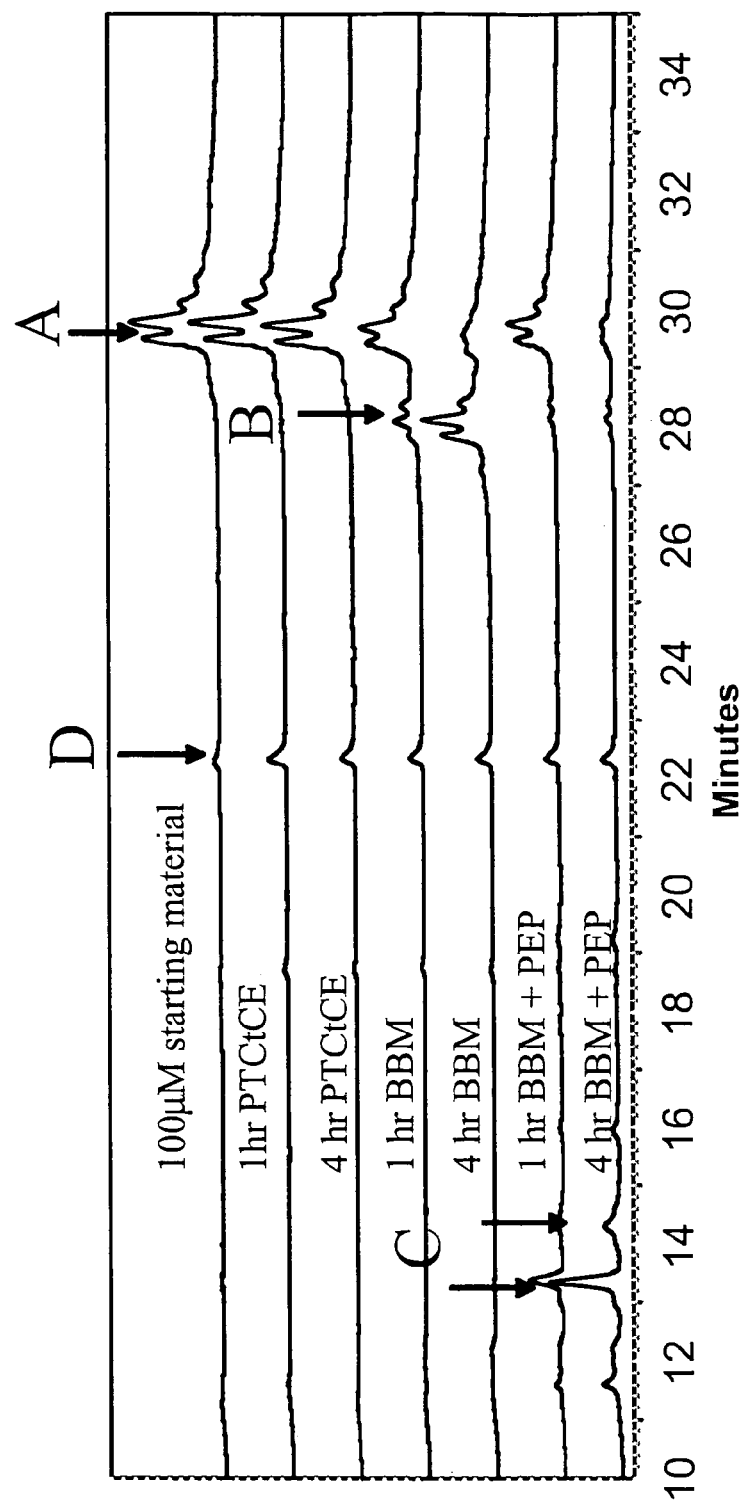
FIG. 1: HPLC traces for in vitro digestion of A) P5. Cleavage of the terminal phenylalanine yields the main digestive product for P5 (B). The addition of PEP enhances the digestive process and small non-immunogenic peptides, (SEQ ID NO:20) PQPQP and (SEQ ID NO:26) QPQLPYP or (SEQ ID NO:23) QLPYPQP, begin to accumulate (C). D) is an artifact of the system and occurred during blank runs as well. (PTCtCE—pepsin, trypsin, chymotrypsin, carboxypeptidase A, and elastase; BBM—brush border membrane; PEP—prolyl endopeptidase.)

Celiac Sprue and/or dermatitis herpetiformis are treated by digestion of gluten oligopeptides contained in foodstuffs consumed by individuals suffering from one or both conditions. Gluten oligopeptides are highly resistant to cleavage by gastric and pancreatic peptidases such as pepsin, trypsin, chymotrypsin, and the like. By providing for digestion of gluten oligopeptides with glutenase, oligopeptides are cleaved into fragments, thereby preventing the disease-causing toxicity.

Methods and compositions are provided for the administration of one or more glutenases inhibitors to a patient suffering from Celiac Sprue and/or dermatitis herpetformis. In some patients, these methods and compositions will allow the patient to ingest glutens without serious health consequences, much the same as individuals that do not suffer from either of these conditions. In some embodiments, the formulations of the invention comprise a glutenase contained in an enteric coating that allows delivery of the active agent(s) to the intestine; in other embodiments, the active agent(s) is stabilized to resist digestion in acidic stomach conditions. In some cases the active agent(s) have hydrolytic activity under acidic pH conditions, and can therefore initiate the proteolytic process on toxic gluten sequences in the stomach itself. Alternative methods of administration provided by the invention include genetic modification of patient cells, e.g. enterocytes, to express increased levels of glutenases; and the introduction of micro-organisms expressing such glutenases so as to transiently or permanently colonize the patient's intestinal tract. Such modified patient cells (which include cells that are not derived from the patient but that are not immunologically rejected when administered to the patient) and microorganisms of the invention are, in some embodiments, formulated in a pharmaceutically acceptable excipient, or introduced in foods. In another embodiment, the invention provides foods pretreated or combined with a glutenase and methods for treating foods to remove the toxic oligopeptides of gluten.

The methods of the invention can be used for prophylactic as well as therapeutic purposes. As used herein, the term "treating" refers both to the prevention of disease and the treatment of a disease or a pre-existing condition. The invention provides a significant advance in the treatment of ongoing disease, to stabilize or improve the clinical symptoms of the patient. Such treatment is desirably performed prior to loss of function in the affected tissues but can also help to restore lost function or prevent further loss of function. Evidence of therapeutic effect may be any diminution in the severity of disease, particularly as measured by the severity of symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like.

Patients that can benefit from the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, e.g. by HLA typing; by family history, by T cell assay, or by other medical means. As is known in the art, dosages may be adjusted for pediatric use.

The present invention relates generally to methods and reagents useful in treating foodstuffs containing gluten with enzymes that digest the oligopeptides toxic to Celiac Sprue patients. Although specific enzymes are exemplified herein, any of a number of alternative enzymes and methods apparent to those of skill in the art upon contemplation of this disclosure are equally applicable and suitable for use in practicing the invention. The methods of the invention, as well as tests to determine their efficacy in a particular patient or application, can be carried out in accordance with the teachings herein using procedures standard in the art. Thus, the practice of the present invention may employ conventional techniques of molecular biology (including recombinant techniques), microbiology, cell biology, biochemistry and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

As used herein, the term "glutenase" refers to an enzyme useful in the methods of the present invention that is capable, alone or in combination with endogenous or exogenously added enzymes, of cleaving toxic oligopeptides of gluten proteins of wheat, barley, oats and rye into non-toxic fragments. Gluten is the protein fraction in cereal dough, which can be subdivided into glutenins and prolamines, which are subclassified as gliadins, secalins, hordeins, and avenins from wheat, rye, barley and oat, respectively. For further discussion of gluten proteins, see the review by Wieser (1996) Acta Paediatr Suppl. 412:3-9, incorporated herein by reference.

In one embodiment, the term "glutenase" as used herein refers to a protease or a peptidase enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "protease" or "peptidase" can refer to a glutenase and as used herein describe a protein or fragment thereof with the capability of cleaving peptide bonds, where the scissile peptide bond may either be terminal or internal in oligopeptides or larger proteins. Prolyl-specific peptidases are glutenases useful in the practice of the present invention.

Glutenases of the invention include protease and peptidase enzymes having at least about 20% sequence identity at the amino acid level, more usually at least about 40% sequence identity, and preferably at least about 70% sequence identity to one of the following peptidases: prolyl endopeptidase (PEP) from *F. meningosepticum* (Genbank accession number D10980), PEP from *A. hydrophila* (Genbank accession number D14005), PEP form *S. capisulata* (Genbank accession number AB010298), DCP I from rabbit (Genbank accession number X62551), DPP IV from *Aspergillus fumigatus* (Genbank accession number U87950) or cysteine proteinase B from *Hordeum vulgare* (Genbank accession number JQ1110).

In one embodiment of the present invention, the glutenase is a PEP. Homology-based identification (for example, by a PILEUP sequence analysis) of prolyl endopeptidases can be routinely performed by those of skill in the art upon contemplation of this disclosure to identify PEPs suitable for use in the methods of the present invention. PEPs are produced in microorganisms, plants and animals. PEPs belong to the serine protease superfamily of enzymes and have a conserved catalytic triad composed of a Ser, His, and Asp residues. Some of these homologs have been characterized, e.g. the enzymes from *F. meningosepticum, Aeromonas hydrophila, Aeromonas punctata, Novosphingobium capsulatum, Pyrococcus furiosus* and from mammalian sources are biochemically characterized PEPs. Others such as the *Nostoc* and *Arabidopsis* enzymes are likely to be PEPs but have not been fully characterized to date. Yet others, such as the *E. coli* and *M. xanthus* enzymes, may not be PEPs but are homologous members of the serine protease superfamily, and can be useful starting materials in protein engineering to make a PEP useful in the practice of the present invention. Relative to the *F. meningoscepticum* enzyme, the pairwise sequence identity of this family of enzymes is in the 30-60% range. Accordingly, PEPs include enzymes having >30% identity to the *F. meningoscepticum* enzyme (as in the *Pyrococcus* enzymes), or having >40% identity (as in the *Novosphingobium* enzymes), or having >50% identity (as in the *Aeromonas* enzymes) to the *F. meningoscepticum* enzyme.

A glutenase of the invention includes a peptidase or protease that has a specific activity of at least 2.5 U/mg, preferably 25 U/mg and more preferably 250 U/mg for cleavage of a peptide comprising one of more of the following motifs: Gly-Pro-pNA, Z-Gly-Pro-pNA (where Z is a benzyloxycarbonyl group), and Hip-His-Leu, where "Hip" is hippuric acid, pNA is para-nitroanilide, and 1 U is the amount of enzyme required to catalyze the turnover of 1 µmole of substrate per minute.

A glutenase of the invention includes an enzyme belonging to any of the following enzyme classifications: EC 3.4.21.26, EC 3.4.14.5, or EC 3.4.15.1.

A glutenase of the invention includes an enzyme having a kcat/Km of at least about 2.5 $s^{-1}$ $M^{-1}$, usually at least about 250 $s^{-1}$ $M^{-1}$ and preferably at least about 25000 $s^{-1}$ $M^{-1}$ for cleavage of any of the following peptides under optimal conditions: (SEQ ID NO:1) QLQPFPQPQLPY, (SEQ ID NO:3) PQPQLPYPQPQLPY, (SEQ ID NO:13) QPQQSFPQQQ, (SEQ ID NO:14) QLQPFPQPELPY, (SEQ ID NO:15) PQPELPYPQPELPY, (SEQ ID NO:16) QPQQSFPEQQ, (SEQ ID NO:5) IQPQQPAQL, (SEQ ID NO:27) QQPQQPYPQ, (SEQ ID NO:28) SQPQQQFPQ, and (SEQ ID NO:10) PFSQQQQPV. A glutenase of the invention includes peptidase or protease having a specificity kcat/Km>2 $mM^{-1}s^{-1}$ for the quenched fluorogenic substrate (SEQ ID NO:2) Abz-QPQQP-Tyr($NO_2$)-D.

A glutenase useful in the practice of the present invention can be identified by its ability to cleave a pretreated substrate to remove toxic gluten oligopeptides, where a "pretreated substrate" is a gliadin, hordein, secalin or avenin protein that has been treated with physiological quantities of gastric and pancreatic proteases, including pepsin (1:100 mass ratio), trypsin (1:100), chymotrypsin (1:100), elastase (1:500), and carboxypeptidases A and B (1:100). Pepsin digestion may be performed at pH 2 for 20 min., to mimic gastric digestion, followed by further treatment of the reaction mixture with trypsin, chymotrypsin, elastase and carboxypeptidase at pH 7 for 1 hour, to mimic duodenal digestion by secreted pancreatic enzymes. The pretreated substrate comprises oligopeptides resistant to digestion, e.g. under physiological conditions.

The ability of a peptidase or protease to cleave a pretreated substrate can be determined by measuring the ability of an enzyme to increase the concentration of free $NH_2$-termini in a reaction mixture containing 1 mg/ml pretreated substrate and 10 µg/ml of the peptidase or protease, incubated at 37° C. for 1 hour. A glutenase useful in the practice of the present invention will increase the concentration of the free amino termini under such conditions, usually by at least about 25%, more usually by at least about 50%, and preferably by at least about 100%. A glutenase includes an enzyme capable of reducing the residual molar concentration of oligopeptides greater than about 1000 Da in a 1 mg/ml "pretreated substrate" after a 1 hour incubation with 10 µg/ml of the enzyme by at least about 2-fold, usually by at least about 5-fold, and preferably by at least about 10-fold. The concentration of such oligopeptides can be estimated by methods known in the art, for example size exclusion chromatography and the like.

A glutenase of the invention includes an enzyme capable of reducing the potency by which a "pretreated substrate" can antagonize binding of (SEQ ID NO:17) PQPELPYPQPQLP to HLA-DQ2. The ability of a substrate to bind to HLA-DQ is indicative of its toxicity; fragments smaller than about 8 amino acids are generally not stably bound to Class II MHC. Treatment with a glutenase that digests toxic oligopeptides, by reducing the concentration of the toxic oligopeptides, prevents a mixture containing them from competing with a test peptide for MHC binding. To test whether a candidate glutenase can be used for purposes of the present invention, a 1 mg/ml solution of "pretreated substrate" may be first incubated with 10 µg/ml of the candidate glutenase, and the ability of the resulting solution to displace radioactive (SEQ ID NO:18) PQPELPYPQPQPLP pre-bound to HLA-DQ2 molecules can then be quantified, with a reduction of displacement, relative to a non-treated control, indicative of utility in the methods of the present invention.

In one embodiment of the invention, methods are provided for determining the therapeutic efficacy of a candidate glutenase enzyme. Methods of interest include in vitro and in vivo screening of enzymes. Such methods may comprise detecting the ability of a candidate enzyme to digest gliadin peptides, including specific peptides provided herein, and determining the ability of the enzyme to digest the peptides to non-toxic fragments. HPLC is optionally utilized to determine the length of digestions products. For determination of pharmacologically useful dosages, in vivo perfusion assays may be utilized.

Polypeptides of interest for such assays include gliadin proteins, fragments of gliadin proteins, and other gluten proteins, preferably peptides resistant to normal digestion. Specific peptides of interest include, without limitation, (P4) (SEQ ID NO:7) LGQQQPFPPQQPYPQPQPF; (P5) (SEQ ID NO:12) LQLQPFPQPQLPYPQPQLPYPQPQLPYPQPQPF; and (P8) (SEQ ID NO:4) FLQPQQPFPQQPQQPYPQQPQQPFPQ. Other peptides resistant to normal digestion may be identified by combining a candidate peptide with one or more of pancreatic enzymes, brush border enzymes, and gastric enzymes, and determining the relative ability of the peptide to resist digestion.

A candidate glutenase, e.g. a prolyl endopeptidase, is combined with one or more digestion-resistant peptides, which may include the above P4, P5 and/or P8. Typically a range of concentrations is used, e.g. at about 1 µU/µL, about 10 µU/µL, about 100 µU/µL, etc. The enzyme may be incubated from about 1 to about 4 hours, and the percentage of parent peptide digested may be calculated by any convenient method. It may be desirable to determine the proteolysis product. HPLC traces are optionally performed to determine the size of digestion products.

In vivo experiments may also be performed, where peptides at physiologically relevant concentrations; peptides and candidate enzymes; peptides and control enzymes, etc. are perfused into an intact intestine in an animal model. The rate of disappearance of peptides is monitored. Data may be collected under conditions where less than about 50% of each peptide disappears, thereby allowing for calculation of steady-state rates of proteolysis. HPLC traces are optionally performed to determine the size of digestion products.

A glutenase of the invention includes an enzyme that reduces the anti-tTG antibody response to a "gluten challenge diet" in a Celiac Sprue patient by at least about 2-fold, more usually by at least about 5-fold, and preferably by at least about 10-fold. A "gluten challenge diet" is defined as the intake of 100 g bread per day for 3 days by an adult Celiac Sprue patient previously on a gluten-free diet. The anti-tTG antibody response can be measured in peripheral blood using standard clinical diagnostic procedures, as known in the art.

Excluded from the term "glutenase" are the following peptidases: human pepsin, human trypsin, human chymotrypsin, human elastase, papaya papain, and pineapple bromelain, and usually excluded are enzymes having greater than 98% sequence identity at the amino acid level to such peptidases, more usually excluded are enzymes having greater than 90% sequence identity at the amino acid level to such peptidases, and preferably excluded are enzymes having greater than 70% sequence identity at the amino acid level to such peptidases.

Among gluten proteins with potential harmful effect to Celiac Sprue patients are included the storage proteins of wheat, species of which include *Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi*; etc. A review of the genes encoding wheat storage proteins may be found in Colot (1990) *Genet Enq* (NY) 12:225-41. Gliadin is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be identified using routine methods of molecular biology. In one aspect of the present invention, genetically modified plants are provided that differ from their naturally occurring counterparts by having gliadin proteins that contain a reduced content of glutamine and proline residues.

Examples of gliadin sequences include but are not limited to wheat alpha gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

For the purposes of the present invention, toxic gliadin oligopeptides are peptides derived during normal human digestion of gliadins and related storage proteins as described above, from dietary cereals, e.g. wheat, rye, barley, and the like. Such oligopeptides are believed to act as antigens for T cells in Celiac Sprue. For binding to Class II MHC proteins, immunogenic peptides are usually from about 8 to 20 amino acids in length, more usually from about 10 to 18 amino acids. Such peptides may include PXP motifs, such as the motif PQPQLP (SEQ ID NO:8). Determination of whether an oligopeptide is immunogenic for a particular patient is readily determined by standard T cell activation and other assays known to those of skill in the art.

As demonstrated herein, during digestion, peptidase resistant oligopeptides remain after exposure of glutens, e.g. gliadin, to normal digestive enzymes. Examples of peptidase resistant oligopeptides are provided. Other examples of immunogenic gliadin oligopeptides are described in Wieser (1995) Baillieres Clin Gastroenterol 9(2):191-207, incorporated herein by reference.

Determination of whether a candidate enzyme will digest a toxic gluten oligopeptide, as discussed above, can be empirically determined. For example, a candidate may be combined with an oligopeptide comprising one or more Gly-Pro-pNA, Z-Gly-Pro-pNA, Hip-His-Leu, Abz-QLP-Tyr($NO_2$)-PQ, Abz-PYPQPQ-Tyr(NO$_2$), PQP-Lys(Abz)-LP-Tyr(NO$_2$)-PQPQLP, PQPQLP-Tyr(NO$_2$)-PQP-Lys(Abz)-LP motifs; with one or more of the oligopeptides (SEQ ID NO:1) QLQPFPQPQLPY, (SEQ ID NO:3) PQPQLPYPQPQLPY, (SEQ ID NO:13) QPQQSFPQQQ, (SEQ ID NO:14) QLQPFPQPELPY, (SEQ ID NO:15) PQPELPYPQPELPY, (SEQ ID NO:16) QPQQSFPEQQ or (SEQ ID NO:12) LQLQPFPQPQLPYPQPQLPYPQPQLPYPQPQPF, (SEQ ID NO:5) IQPQQPAQL, (SEQ ID NO:27) QQPQQPYPQ, (SEQ ID NO:28) SQPQQQFPQ, and (SEQ ID NO:10) PFSQQQQPV; or with a pretreated substrate comprising one or more of gliadin, hordein, secalin or avenin proteins that have been treated with physiological quantities of gastric and pancreatic proteases. In each instance, the candidate is determined to be a glutenase of the invention if it is capable of cleaving the oligopeptide. Glutenases that have a low toxicity for human cells and are active in the physiologic conditions present in the intestinal brush border are preferred for use in some applications of the invention, and therefore it may be useful to screen for such properties in candidate glutenases.

The oligopeptide or protein substrates for such assays may be prepared in accordance with conventional techniques, such as synthesis, recombinant techniques, isolation from natural sources, or the like. For example, solid-phase peptide synthesis involves the successive addition of amino acids to create a linear peptide chain (see Merrifield (1963) J. Am. Chem. Soc. 85:2149-2154). Recombinant DNA technology can also be used to produce the peptide.

Candidate glutenases for use in the practice of the present invention can be obtained from a wide variety of sources, including libraries of natural and synthetic proteins. For example, numerous means are available for random and directed mutation of proteins. Alternatively, libraries of natural proteins in the form of bacterial, fungal, plant and animal extracts are available or readily produced. Extracts of germinating wheat and other grasses is of interest as a source of candidate enzymes. Natural or synthetically produced libraries and compounds are readily modified through conventional chemical, physical and biochemical means, and such means can be used to produce combinatorial libraries. Known pharmacological agents may be subjected to directed or random chemical modifications, such as acylation, alkylation, esterification, and amidification, to produce structural analogs of proteins.

Generally, a variety of assay mixtures are run in parallel with different peptidase concentrations to obtain a differential response to the various concentrations. Typically, one of these concentrations serves as a negative control, i.e. at zero concentration or below the level of detection. A variety of other reagents may be included in a screening assay. These include reagents like salts, detergents, and the like that are used to facilitate optimal activity and/or reduce non-specific or background interactions. Reagents that improve the efficiency of the assay may be used. The mixture of components is added in any order that provides for the requisite activity. Incubations are performed at any suitable temperature, typically between 4 and 40° C. Incubation periods are selected for optimum activity but can also be optimized to facilitate rapid high-throughput screening or other purposes. Typically, between 0.1 and 1 hours will be sufficient.

The level of digestion of the toxic oligopeptide can be compared to a baseline value. The disappearance of the starting material and/or the presence of digestion products can be monitored by conventional methods. For example, a detectable marker can be conjugated to a peptide, and the change in molecular weight associated with the marker is then determined, e.g. acid precipitation, molecular weight exclusion, and the like. The baseline value can be a value for a control sample or a statistical value that is representative a control population. Various controls can be conducted to ensure that an observed activity is authentic, including running parallel reactions, positive and negative controls, dose response, and the like.

Active glutenases identified by the screening methods described herein can serve as lead compounds for the synthesis of analog compounds to identify glutenases with improved properties. Identification of analog compounds can be performed through use of techniques such as self-consistent field (SCF) analysis, configuration interaction (CI) analysis, and normal mode dynamics analysis.

In one embodiment of the invention, the glutenase is a prolyl endopeptidase (PEP, EC 3.4.21.26). Prolyl endopeptidases are widely distributed in microorganisms, plants and animals, and have been cloned from *Flavobacterium meningosepticum*, (Yoshimoto et al. (1991) *J. Biochem.* 110, 873-8); *Aeromonas hydrophyla* (Kanatani et al. (1993) *J. Biochem.* 113, 790-6); *Sphingomonas capsulata* (Kabashima et al. (1998) *Arch. Biochem. Biophys.* 358, 141-148), *Pyrococcus furious* (Robinson et al. (1995) *Gene* 152, 103-6); pig (Rennex et al. (1991) *Biochemistry* 30, 2195-2030); and the like. The suitability of a particular enzyme is readily determined by the assays described above, by clinical testing; determination of stability in formulations, and the like. Other sources of PEP include *Lactobacilli* (Habibi-Najafi et al. (1994) J. Dairy Sci. 77, 385-392), from where the gene of interest can be readily cloned based on sequence homology to the above PEP's or via standard reverse genetic procedures involving purification, amino-acid sequencing, reverse translation, and cloning of the gene encoding the target extracellular enzyme.

In another embodiment of the invention, glutenases are peptidases present in the brush border, which are supplemented. Formulations of interest may comprise such enzymes in combination with other peptidases. Peptidases present in brush border include dipeptidyl peptidase IV (DPP IV, EC 3.4.14.5), and dipeptidyl carboxypeptidase (DCP, EC 3.4.15.1). The human form of these proteins may be used, or modified forms may be isolated from other suitable sources. Example of DPP IV enzymes include *Aspergillus* spp. (e.g. Byun et al. (2001) J. Agric. Food Chem. 49, 2061-2063), ruminant bacteria such as *Prevotella albensis* M384 (NCBI protein database Locus # CAC42932), dental bacteria such as *Porphyromonas gingivalis* W83 (Kumugai et al. (2000) Infect. Immun. 68, 716-724), lactobacilli such as *Lactobacillus helveticus* (e.g. Vesanto, et al, (1995) Microbiol. 141, 3067-3075), and *Lactococcus lactis* (Mayo et al., (1991) Appl. Environ. Microbiol. 57, 38-44). Other DPP IV candidates can readily be recognized based on homology to the above enzymes, preferably >30% sequence identity. Similarly, secreted dipeptidyl carboxypeptidases that cleave C-terminal X-Pro sequences are found in many microbial sources including *Pseudomonas* spp (e.g. Ogasawara et al, (1997) Biosci. Biotechnol. Biochem. 61, 858-863), *Streptomyces* spp. (e.g. Miyoshi et al., (1992) J. Biochem. 112, 253-257) and *Aspergilli* spp. (e.g. Ichishima et al., (1977) J. Biochem. 81, 1733-1737). Of particular interest is the enzyme from *Aspergillus saitoi* (Ichishima), due to its high activity at acidic pH values. Although the genes encoding many of these enzymes have not yet been cloned, they can be readily cloned by standard reverse genetic procedures. The DCP I enzymes can be purified from the extracellular medium based on their ability to hydrolyze (SEQ ID NO:19) Z-Gly-Pro-Leu-Gly-Pro, Z-Gly-Pro, or Hip-Gly-Pro. Alternatively, putative DCP I genes can be identified based on homology to the *E. coli* enzyme (NCBI protein database Locus CAA41014.)

In another embodiment of the invention, glutenases are endoproteases found in developing grains of toxic cereals such as wheat, barley and rye. For example, Dominguez and Cejudo (Plant Physiol. 112, 1211-1217, 1996) have shown that the endosperm of wheat (i.e. the part of the grain that contains gliadin and glutenin) contains a variety of neutral and acid proteases. Although these proteases have not been individually characterized, they are expected to be an especially rich source of glutenases. Moreover, although the genes encoding these proteases have not yet been cloned, Dominguez and Cejudo have established a convenient SDS-PAGE assay for identification and separation of these proteases. After excision of the corresponding protein bands from the gel, limited sequence information can be obtained. The cDNA encoding these proteases can therefore be readily cloned from this information using established reverse genetic procedures, and expressed in heterologous bacterial or fungal hosts. Of particular interest are proteases that hydrolyze α2-gliadin within the 33-mer amino acid sequence identified in Example 2 below. Of further interest are the subset of these proteases that retain activity at acidic pH values (pH2-5) encountered in the stomach.

The amino acid sequence of a glutenase, e.g. a naturally occurring glutenase, can be altered in various ways known in the art to generate targeted changes in sequence and additional glutenase enzymes useful in the formulations and compositions of the invention. Such variants will typically be functionally-preserved variants, which differ, usually in sequence, from the corresponding native or parent protein but still retain the desired biological activity. Variants also include fragments of a glutenase that retain enzymatic activity. Various methods known in the art can be used to generate targeted changes, e.g: phage display in combination with random and targeted mutations, introduction of scanning mutations, and the like.

A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine).

Glutenase fragments of interest include fragments of at least about 20 contiguous amino acids, more usually at least about 50 contiguous amino acids, and may comprise 100 or more amino acids, up to the complete protein, and may extend further to comprise additional sequences. In each case, the key criterion is whether the fragment retains the ability to digest the toxic oligopeptides that contribute to the symptoms of Celiac Sprue.

Modifications of interest that do not alter primary sequence include chemical derivatization of proteins, e.g., acetylation or carboxylation. Also included are modifications of glycosylation, e.g. those made by modifying the glycosylation patterns of a protein during its synthesis and processing or in further processing steps; e.g. by exposing the protein to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Also useful in the practice of the present invention are proteins that have been modified using molecular biological techniques and/or chemistry so as to improve their resistance to proteolytic degradation and/or to acidic conditions such as those found in the stomach, and to optimize solubility properties or to render them more suitable as a therapeutic agent. For example, the backbone of the peptidase can be cyclized to enhance stability (see Friedler et al. (2000) *J. Biol. Chem.* 275:23783-23789). Analogs of such proteins include those containing residues other than naturally occurring L-amino acids, e.g. D-amino acids or non-naturally occurring synthetic amino acids.

The glutenase proteins of the present invention may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. Using synthesizers, one can readily substitute for the naturally occurring amino acids one or more unnatural amino acids. The particular sequence and the manner of preparation will be determined by convenience, economics, purity required, and the like. If desired, various groups can be introduced into the protein during synthesis that allow for linking to other molecules or to a surface. For example, cysteines can be used to make thioethers, histidines can be used for linking to a metal ion complex, carboxyl groups can be used for forming amides or esters, amino groups can be used for forming amides, and the like.

The glutenase proteins useful in the practice of the present invention may also be isolated and purified in accordance with conventional methods from recombinant production systems and from natural sources. A lysate can be prepared from the expression host and the lysate purified using HPLC, exclusion chromatography, gel electrophoresis, affinity chromatography, and/or other purification techniques. Typically, the compositions used in the practice of the invention will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one aspect, the present invention provides a purified preparation of a glutenase. Prior to the present invention, there was no need for a glutenase that could be ingested by a human or mixed with a foodstuff. Thus, prior to the present invention most glutenases did not exist in a form free of contaminants that could be deleterious to a human if ingested. The present invention creates a need for such glutenase preparations and provides them and methods for preparing them. In a related embodiment, the present invention provides novel foodstuffs that are derived from gluten-containing foodstuffs but have been treated to reduce the concentration and amount of the oligopeptides and oligopeptide sequences discovered to be toxic to Celiac Sprue patients. While gluten-free or reduced-gluten content foods have been made, the foodstuffs of the present invention differ from such foodstuffs not only by the manner in which they are prepared, by treatment of the foodstuff with a glutenase, but also by their content, as the methods of the prior art result in alteration of non-toxic (to Celiac Sprue patients) components of the foodstuff, resulting in a different taste and composition. Prior art foodstuffs include, for example, Codex Alimentarius wheat starch, which is available in Europe and has <100 ppm gluten. The starch is usually prepared by processes that take advantage of the fact that gluten is insoluble in water whereas starch is soluble.

In one embodiment of the present invention, a Celiac Sprue patient is, in addition to being provided a glutenase or food treated in accordance with the present methods, provided an inhibitor of tissue transglutaminase, an anti-inflammatory agent, an anti-ulcer agent, a mast cell-stabilizing agents, and/or and an-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

As used herein, compounds which are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds useful for co-administration with the glutenases and treated foodstuffs of the invention can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. 0. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-lnterscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

The glutenase proteins of the invention and/or the compounds administered therewith are incorporated into a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the glutenase and/or other compounds can be achieved in various ways, usually by oral administration. The glutenase and/or other compounds may be systemic after administration or may be localized by virtue of the formulation, or by the use of an implant that acts to retain the active dose at the site of implantation.

In pharmaceutical dosage forms, the glutenase and/or other compounds may be administered in the form of their pharmaceutically acceptable salts, or they may also be used alone or in appropriate association, as well as in combination with other pharmaceutically active compounds. The agents may be combined, as previously described, to provide a cocktail of activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71 (3):307-18.

In another embodiment, a microorganism, for example bacterial or yeast culture, capable of producing glutenase is administered to a patient. Such a culture may be formulated as an enteric capsule; for example, see U.S. Pat. No. 6,008,027, incorporated herein by reference. Alternatively, microorganisms stable to stomach acidity can be administered in a capsule, or admixed with food preparations.

In another embodiment, the glutenase is admixed with food, or used to pre-treat foodstuffs containing glutens. Glutenase present in foods can be enzymatically active prior to or during ingestion, and may be encapsulated or otherwise treated to control the timing of activity. Alternatively, the glutenase may be encapsulated to achieve a timed release after ingestion, e.g. in the intestinal tract.

Formulations are typically provided in a unit dosage form, where the term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Depending on the patient and condition being treated and on the administration route, the glutenase may be administered in dosages of 0.01 mg to 500 mg/kg body weight per day, e.g. about 20 mg/day for an average person. A typical dose of glutenase in patients will be in at least about 1 mg/adult, more usually at least about 10 mg; and preferably at least about 50 mg; usually not more than about 5 g, more usually not more than about 1 g, and preferably not more than about 500 mg. Dosages will be appropriately adjusted for pediatric formulation. In children the effective dose may be lower, for example at least about 0.1 mg, or 0.5 mg. In combination therapy involving, for example, a PEP+DPP IV or PEP+ DCP I, a comparable dose of the two enzymes may be given; however, the ratio will be influenced by the relative stability of the two enzymes toward gastric and duodenal inactivation.

Those of skill will readily appreciate that dose levels can vary as a function of the specific enzyme, the severity of the symptoms and the susceptibility of the subject to side effects. Some of the glutenases are more potent than others. Preferred dosages for a given enzyme are readily determinable by those of skill in the art by a variety of means. A preferred means is to measure the physiological potency of a given compound.

Other formulations of interest include formulations of DNA encoding glutenases of interest, so as to target intestinal cells for genetic modification. For example, see U.S. Pat. No. 6,258,789, herein incorporated by reference, which discloses the genetic alteration of intestinal epithelial cells.

The methods of the invention are used to treat foods to be consumed or that are consumed by individuals suffering from Celiac Sprue and/or dermatitis herpetiformis by delivering an effective dose of glutenase. If the glutenase is administered directly to a human, then the active agent(s) are contained in a pharmaceutical formulation. Alternatively, the desired effects can be obtained by incorporating glutenase into food products or by administering live organisms that express glutenase, and the like. Diagnosis of suitable patients may utilize a variety of criteria known to those of skill in the art. A quantitative increase in antibodies specific for gliadin, and/or tissue transglutaminase is indicative of the disease. Family histories and the presence of the HLA alleles HLA-DQ2 [DQ(a1*0501, b1*02)] and/or DQ8 [DQ(a1*0301, b1*0302)] are indicative of a susceptibility to the disease.

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease.

Various methods for administration may be employed, preferably using oral administration, for example with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

EXAMPLE 1

By comparing the in vitro and in vivo digestion of a panel of structurally diverse γ- and β-gliadin derived peptides that are believed to induce toxic effects in Celiac Sprue, we were able to quantify their relative resistance to digestion. The experimentally measured parameters were used to develop a quantitative model for the luminal content of gliadin peptides in the human intestine. Our findings indicate that toxic gliadin peptides persist ~4-8 times longer in the intestine than physiologically relevant controls from low-proline fractions of gliadin or from myoglobin. Quantitative analysis of in vivo prolyl endopeptidase (PEP) supplementation demonstrated that resistant gliadin peptides could be effectively proteolyzed at rates comparable to non-immunogenic control peptides.

Methods

Materials

A summary of the peptides used in the following experiments, the source, and peptide identifiers can be found in Table 1. Throughout this report peptides are identified by their sequences or numerical peptide identifiers. Purity of all peptides was verified by reverse phase C-18 HPLC. (SEQ ID NO:12) LQLQPFPQPQLPYPQPQLPYPQPQLPYPQPQPF was found to contain the related 32-mer devoid of the N-terminal Leu residue, (SEQ ID NO:25) QLQPF-PQPQLPYPQPQLPYPQPQLPYPQPQPF, as well as smaller quantities of (SEQ ID NO:22) Pyro-QLQPF-PQPQLPYPQPQLPYPQPQLPYPQPQPF, and consequently appears as a dimmer in HPLC traces. All of the enzymes were purchased from Sigma (St. Louis, Mo.) except *Flavobacterium meningosepticum* prolyl endopeptidase, which was purchased from United States Biological (Swampscott, Ma.). Alternatively, the same enzyme was prepared from recombinant *E. coli*; and its activity was comparable to commercially available PEP.

intestinal brush border enzymes, where the final concentration of brush border aminopeptidase N was 100 µU/µL. The rat intestinal brush border was prepared as described (Ahnen et al., 1982) and the activity was measured by assaying continuously at 30° C. in 0.1 M Tris HCl, pH 8.0, containing 1 mM Leu-pNA [extinction coefficient at 410 nm (ε410)=8,800 $M^{-1}/cm^{-1}$] in 1% dimethyl sulfoxide to improve solubility. In some reactions prolyl endopeptidase was also added at a final concentration of 100 µU/µL. The reaction mixture was analyzed by reverse phase HPLC on a Vydac 218MS54 column (4.6 mm inner diameter×15 cm).

In vivo Rat Intestinal Perfusion. Our procedure for in vivo intestinal perfusion of peptides in rats was modified from the Smithson and Gray procedure as follows: Sprague-Dawley rats, 250-350 g were anesthetized with isoflurane, the abdomen opened, the ligament of Treitz (duodenal-jejunal junction) identified and polyethylene catheters [2.5 mm outer diameter×1 mm inner diameter] were installed with the proximal infusion catheter placed 5 cm beyond the ligament of Treitz and the collection catheter positioned 20 cm distally. Animal core temperature was monitored to be at 37° C. by rectal thermometer. Peptides for intra-intestinal perfusion were 1 mM GLGG, 0.1 mM P3, 0.1 mM P4, 0.1 mM P5, 0.1 mM P8, 0.1 mM P9, and 0.1 mM P10. The peptides were dissolved in 154 mM NaCl and perfused at 0.3-0.4 mL/min for 15 minutes to achieve a steady state for collection at the

TABLE 1

Peptides, peptide identifier, and source.

| Idenfifier | PEPTIDE SEQUENCE | | SOURCE |
|---|---|---|---|
| P1 | GLGG | | Bachem (Torrance, CA) |
| P2 | QLQPFPQPQLPY[a] | (SEQ ID NO:1) | New England Peptide (Fitchburg, MA) |
| P3 | PQPQLPYPQPQLP[a] | (SEQ ID NO:11) | Pepscan (Belgium) |
| P4 | LGQQQPFPPQQPYPQPQPF[b] | (SEQ ID NO:7) | New England Peptide (Fitchburg, MA) |
| P5 | LQLQPFPQPQLPYPQPQLPYPQPQLPYPQPQPF[c] | (SEQ ID NO:12) | Boc-synthesis |
| P6 | VSFQQPQQQYPSSQ[d] | (SEQ ID NO:29) | Pepscan (Belgium). |
| P7 | PQQPQQSFPQQQRP[e] | (SEQ ID NO:21) | Boc-synthesis |
| P8 | FLQPQQPFPQQPQQPYPQQPQQPFPQ | (SEQ ID NO:4) | Stanford PAN Facility (Stanford, CA) |
| P9 | WQIPEQSR[e] | (SEQ ID NO:30) | Stanford PAN Facility (Standord, CA). |
| P10 | KGHHEAELKPL | (SEQ ID NO:6) | Stanford PAN Facility (Stanford, CA) |

[a]Arentz-Hansen et al., 2000
[b]De Ritis et al., 1988
[c]Shan et al., 2002
[d]Novák et al., 2002
[e]Molberg et al., 1998

In vitro Digestion of Gliadin Peptides. The in vitro digestion of each peptide was performed as follows: 75 µM (final concentration) of peptide was combined with 32 µL of 0.03 M HCl, pepsin (1:100 w pepsin/w peptide) and water to give a volume of 104 µL. The reaction was carried out for 30 minutes at 37° C. and was stopped by the addition of 40 µL of 1M sodium phosphate/sodium bisphosphate (pH 7.04). Chymotrypsin (1:100 w/w), trypsin (1:100.7 w/w), elastase (1:200 w/w), and carboxypeptidase A (1:100 w/w) were then added to give a final reaction volume of 168 µL. The reaction mixture was incubated at 37° C. for the indicated time and then stopped by heating at 90° C. for 5 minutes. Alternatively, the peptide (75M final concentration) was combined with rat distal catheter. For each PEP supplemented digestion, a solution of 50 µU/µL PEP in 154 mM NaCl and a separate 0.2 mM solution of the appropriate peptide were perfused through separate tubes at 0.2 mL/min and then combined at the infusion port producing a total flow rate of 0.4 mL/min to achieve 0.1 mM peptide, and 25 µU/µL PEP. The residence time of the perfusate in the intestinal lumen was approximately 10 min. Additional experiments were performed to determine dose dependence of P5 digestion by perfusing 0.05 mM P5 with recombinant PEP at concentrations from 5.6-41.7 µU/µL (~25-190 µU/µL).

In a separate experiment, pepsin, trypsin and chymotrypsin digested gliadin (Sigma, St. Louis, Mo.) was perfused at 2 mg/mL along with 0.05 mM P5 and 41.7 µU/µL recombinant PEP (~190 µU/µL) to determine the effect of smaller, more accessible peptide fragments on P5 digestion. The perfusion effluent was collected, immediately frozen and subsequently analyzed by reverse phase HPLC on a Vydac 218MS54 column (4.6 mm inner diameter×15 cm). The rate of substrate disappearance for the peptides was calculated as previously detailed (Smithson and Gray, 1977). It is important to note that the in vivo experiments presented here are designed to represent the physiological assimilation of gliadin peptides that are end products of pancreatic protease digestion. Consequently, our perfusion model has been simplified to exclude the effects of endogenous pancreatic enzymes and pancreatic protein secretions. We recognize that pancreatic enzymes are likely to degrade orally administered PEP, and additional intestinal luminal proteins are likely to compete with the PEP's ability to proteolyze P5. However, our intention at this stage of the work was not to establish the stability of PEP to pancreatic digestion, but instead to understand quantitatively the resistance of potentially toxic gliadin peptides to brush border proteolysis, as well as the effect of PEP supplementation on this process under ideal intra-intestinal conditions.

Mathematical Modeling of Intestinal Content of Toxic Gliadin Peptides. The in vivo data presented in this report was used to estimate the luminal content of plugs of gliadin peptides P4 and P5 as they progress through the small intestinal tract. The beneficial effect of PEP supplementation on P5 processing was also analyzed in a similar manner. In this analysis the length and diameter of the human small intestine were assumed to be 5 m and 3.8 cm, respectively, and the transit time of a peptide plug across this distance was estimated as 4 h. For analytical purposes the intestine was divided into 240 segments of ~2.1 cm length each, such that each segment corresponded to the distance traversed per minute. To estimate the peptide concentration, $c_i$, that exits each segment i, it is first necessary to determine the rate constant, k, for intestinal brush border membrane catalyzed proteolysis of each peptide. The rate constant k was assumed to be first order, which would be the case if the Michaelis-Menten parameter $K_M >> [S]$. This assumption was validated for GLGG (a peptide easily digested by intestinal brush border peptidases) in an earlier study. The rate constant k was calculated in an iterative manner for each peptide. The correct k value was that at which the calculated surface rate of peptide proteolysis (i.e. moles peptide per unit surface area per unit time) was 4× that observed experimentally in the rat intestinal perfusion loop. (The surface area in the human small intestine is 300-fold greater than that of a smooth cylindrical tube, whereas the surface area of the rat small intestine is 75-fold higher than that of a smooth tube. It should be noted that these surface rates of peptide proteolysis are substantially greater (>8×) than the rate of movement across the epithelium). Consequently, the flux of peptide across the epithelium could be safely ignored in this study without affecting its conclusions.

Results

Digestive resistance of gliadin peptides and effect of PEP. The gliadin peptides P2-P8 (Table 1) were incubated with pepsin, trypsin, chymotrypsin, carboxypeptidase A, and elastase (PTCtCE) and purified rat intestinal brush border membranes (BBM) as previously detailed (Shan et al., 2002) to assess their resistance to digestion. Each peptide is derived from α or γ-gliadin sequences, and has been shown to exhibit toxicity. Peptides P2, P3, P5 contain one or more epitopes from α-gliadin, whereas P7 and P8 carry γ-gliadin epitopes. P4 is believed to stimulate the innate immune system, and P6 has macrophage stimulating activity.

The results summarized in Table 2 clearly indicate an unusual degree of resistance to digestion by gastric and pancreatic enzymes for all of the peptides tested except P6. In contrast, exposure to the BBMs revealed substantial cleavage for some of the peptides, but very little or no digestion for others. With the exception of P5 and P8, a recently identified resistant fragment from γ-gliadin, all of the peptides were digested by the peptidases of the intestinal surface (BBM) to levels below 20% of the starting material, but four hours of exposure to brush border membrane preparations were required for processing of most of the gliadin peptides. Such a prolonged exposure to the brush border surface may not occur under typical physiological conditions.

Given the stability of gliadin peptides to intestinal peptidases and initial results indicating PEP is active against α-gliadin epitopes, the efficacy of in vitro digestion with PEP was examined. To quantify the incremental effect of PEP, we incubated the gliadin peptides with purified brush border membranes, supplemented with 100 µU/µL of PEP for 1 or 4 hours at 37° C. Some of the gliadin peptides (most notably P2 and P6) were processed efficiently by the BBM peptidases; in these cases the incremental effect of adding PEP was marginal (Table 2).

TABLE 2

In vitro digestion of gliadin peptides

| Peptide Identifier | PTCtCE 4 hr | BBM 1 hr | BBM 4 hr | BBM + PEP 1 hr | BBM + PEP 4 hr |
|---|---|---|---|---|---|
| P2 | 1 | 71 | 94 | 80 | 99 |
| P3 | NR | 36 | 94 | 63 | 95 |
| P4 | NR | 77 | 98 | 99 | 99 |
| P5 | 10 | 20 | 28 | 44 | 91 |
| P6 | 48 | 97 | 99 | 99 | 99 |
| P7 | 4 | 70 | 89 | 74 | 89 |
| P8 | 13 | NR | 19 | >99 | >99 |

In vitro digestion data for selected gliadin peptides presented as the percentage of parent material digested. For reaction conditions, see Methods. (PTCtCE—pepsin, trypsin, chymotrypsin, carboxypeptidase A, and elastase; BBM—brush border membrane; NR—no reaction.)

In contrast, a dramatic supplemental effect of PEP was observed on the digestion of the highly immunogenic P5 peptide and the newly discovered P8 peptide. It should be noted that these analyses of parent peptide disappearance only provide data on the initial step of processing, and it is important to also consider the putative toxic capacity of the smaller proteolysis products. HPLC traces of the in vitro digestion indicate brush border peptidases are capable of removing only the C-terminal Phe residue from P5, illustrating that there is enhanced digestion of P5 by PEP to smaller peptides (FIG. 1). The intermediates for P5 were determined by LC-MS-MS to be the non-toxic peptides (SEQ ID NO:20) PQPQP and (SEQ ID NO:26) QPQLPYP or (SEQ. ID NO:23) QLPYPQP. Thus, PEP appears to facilitate the digestion of brush border resistant gliadin peptides by generating smaller products that are either non-toxic or are then substrates for the BB peptidases. Disappearance of gliadin peptides in intact rat intestine—a process independent of peptide length.

To verify the in vitro stability of some gliadin-derived peptides to digestion by rat intestinal surface peptidases, we performed a series of in vivo peptide digestion experiments. Peptides were perfused at physiologically relevant concentrations via a catheter placed 5 cm distal to the ligament of Treitz and samples were collected from a catheter positioned 20 cm distally. The peptide GLGG, known to be efficiently assimilated by the small intestine, was used as a control to determine variations between rats and as a standard to compare with previously published data. GLGG was perfused at the beginning and end of each experiment to determine any loss of in vivo digestive capacity during the in vivo procedure. The rate of GLGG disappearance was determined to be 74±7 pmol/cm$^2$ sec at the beginning of the perfusion experiment, and this disappearance rate did decline at the end of the experiment to 49±5 pmol/cm$^2$ sec.

Figure 2:
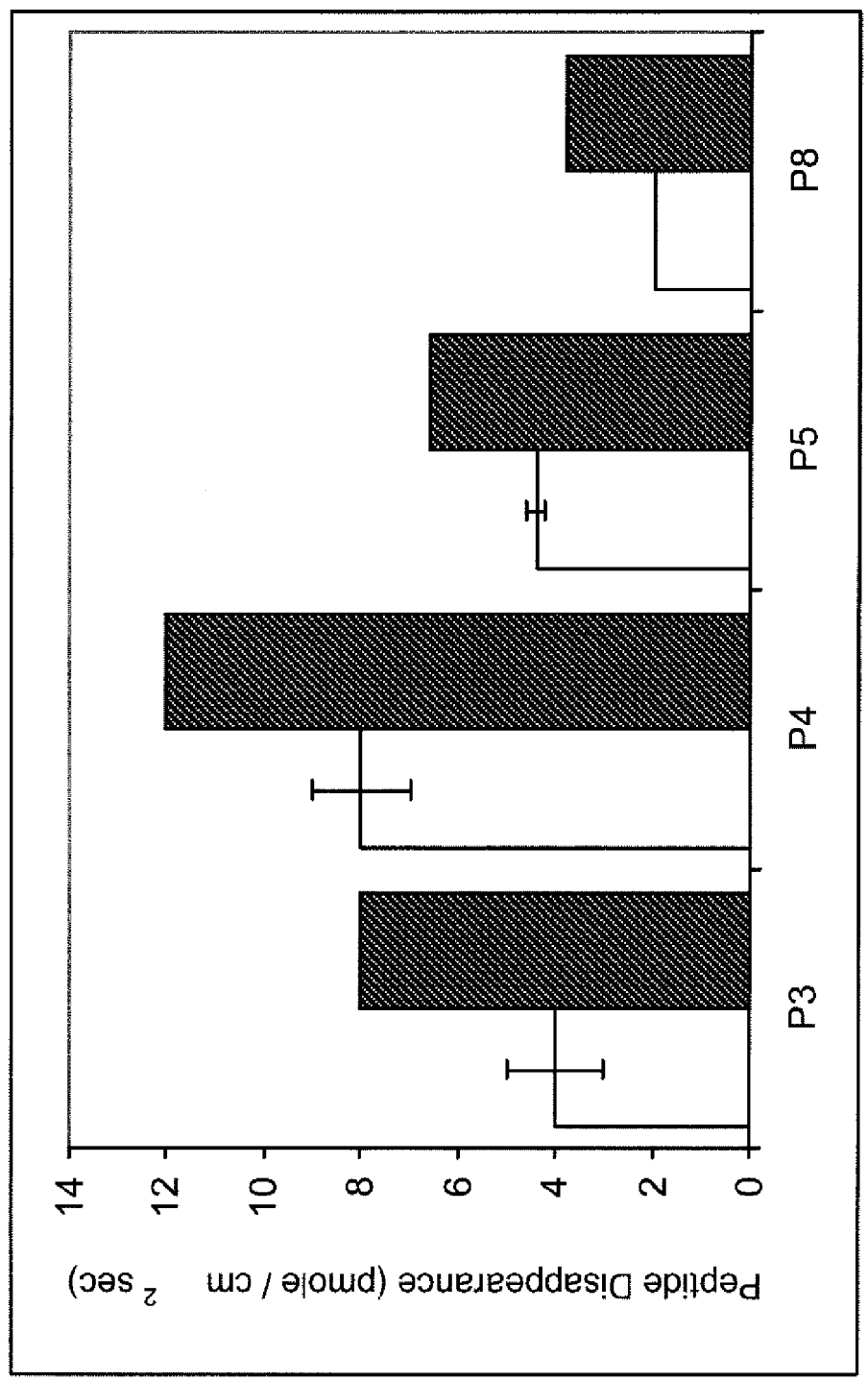
FIG. 2: Rate of digestion for in vivo rat intestinal perfusion of P3, P4, P5, and P8. GLGG, P9, and P10 were measured at 74, 21, and 18 (pmol/cm 2 sec), respectively. [Light gray bars—no prolyl endopeptidase and dark gray bars—with prolyl endopeptidase.].

FIG. 2 shows the rate of disappearance for the gliadin derived peptides, P3, P4 and P5, as determined by three different peptide perfusion experiments taking into account the decline, assumed to be linear, in intestinal capacity over the period of the experiment, as detailed above. Also included in FIG. 2 is the rate data for P8. P10 (a product of pepsin and pancreatic protease digestion of myoglobin) and P9 (a product of pepsin and pancreatic protease digestion of α-gliadin that lacks immunogenicity) were used as physiologically relevant controls to determine if the size of the peptide plays a role in digestion. There currently are no known physiologically relevant controls available for comparison with P5 and P8 peptides. The proteolysis rates for P10 and P9 were 18 and 21 pmol/cm 2 sec, respectively. All data were collected under conditions where <50% of each peptide disappeared, thereby allowing for calculation of steady-state rates of proteolysis. Together with the in vitro data in Table 1, these results establish that immunogenic gliadin peptides such as P4, P5 and P8 are not only resistant to digestion with gastric and pancreatic enzymes, but they also display a relative resistance to digestion by the brush border enzymes as compared to non-toxic dietary peptides such as P10 and P9.

Figure 3:
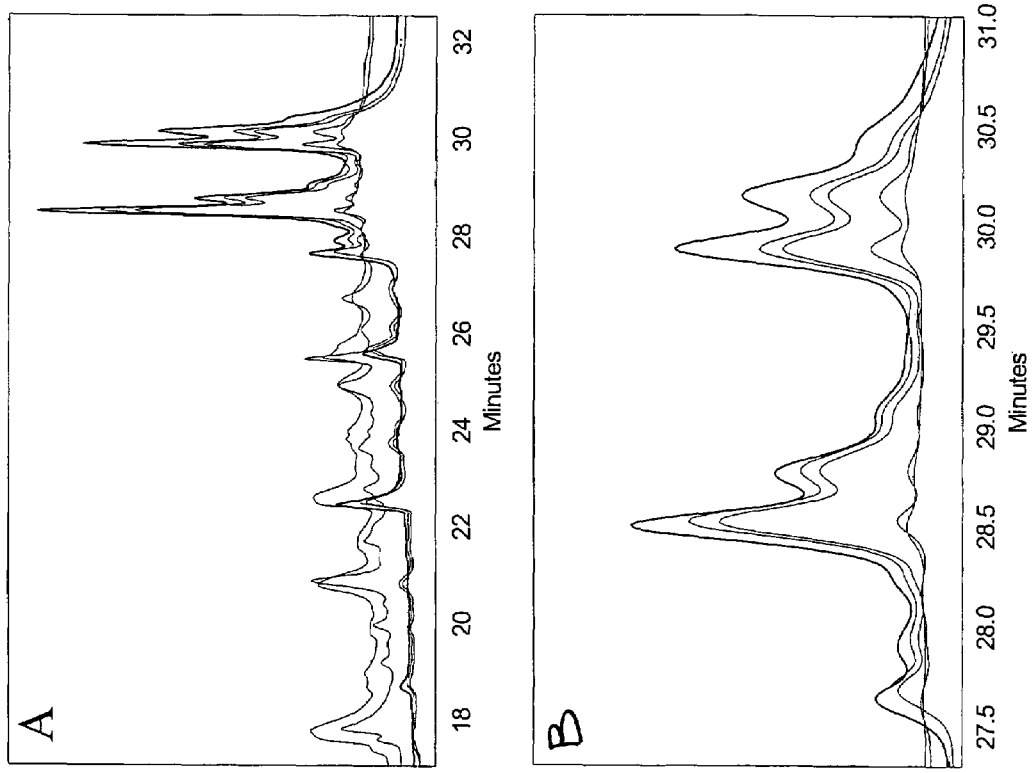
FIGS. 3A-3B: In vivo prolyl endopeptidase (PEP) dose dependent digestion of P5. The entire HPLC trace is shown above (A). The amount of remaining P5 is shown below: B) 0.0, C) 25 µU/µL, D) 65 µU/µL, E) 125 µU/µL, F) 155 µU/µL and G) 190 µU/µL recombinant PEP.

To further explore the capacity of PEP to enhance gliadin digestion, we measured PEP supplemental proteolysis of the gliadin peptides in vivo by co-perfusing the gliadin peptides with PEP, 25 μU/μL, under the same conditions as detailed above. The rate of digestion was increased significantly, 50%-100%, for each gliadin-derived peptide, as shown in FIG. 2, but there was no detectable change in the rate of the control peptide (GLGG) digestion. HPLC analysis verified the increased digestion of the otherwise resistant gliadin peptides. Digestion of P3 produced the resistant intermediate, (SEQ ID NO:8) PQPQLP (Hausch et al., 2002). No other digestive intermediates were identified for the other gliadin peptides. To determine the amount of PEP required to eliminate P5 under the perfusion conditions described under Methods, the concentration of recombinant PEP co-perfused with 50 μM P5 was systematically increased (FIG. 3). A dose-dependent reduction of P5 was observed in this experiment with virtually all of the starting material eliminated in the presence of 41.7 μg/ml PEP (~190 μU/μL). This dose corresponds to ca. 1:5 weight ratio for PEP:P5. Under these conditions three intermediates were observed to accumulate to ~10% of the starting material. Thus, supplementation of exogenous recombinant PEP in the jejunum can result in rapid digestion of highly proteolysis resistant gliadin peptides such as P5.

Figure 4:
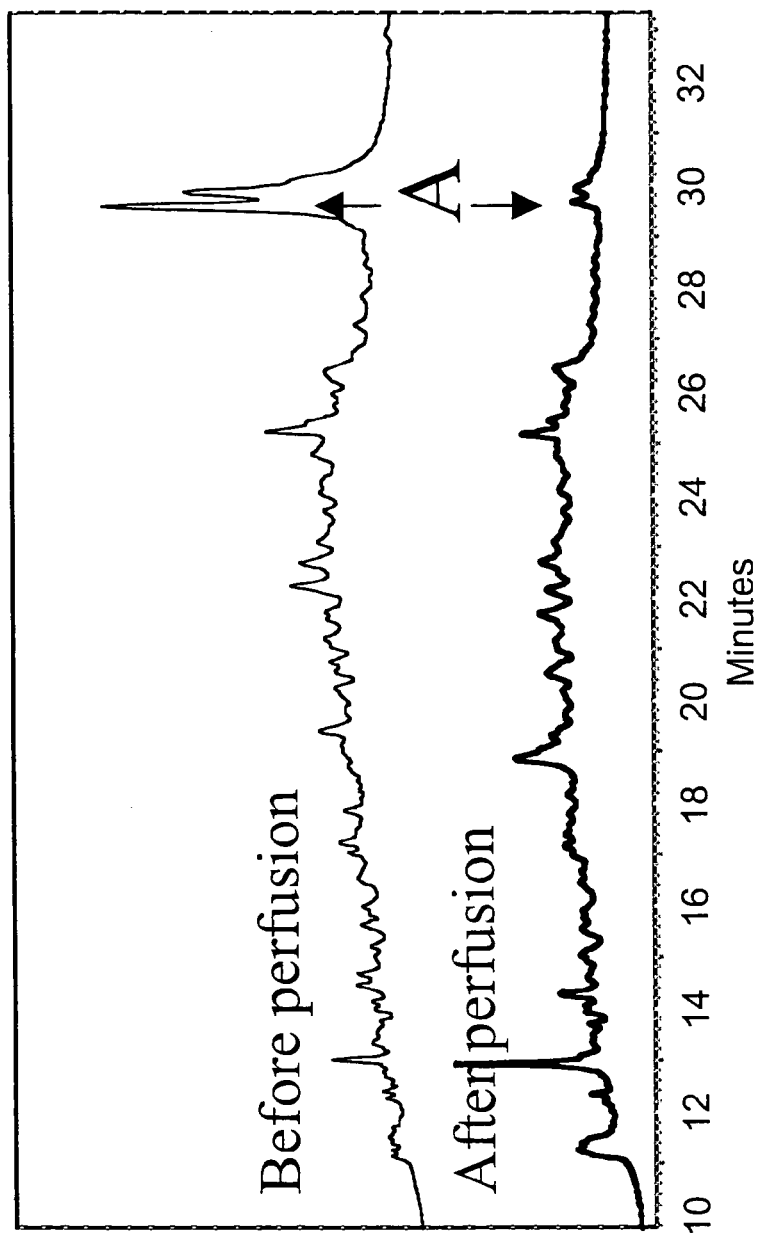
FIG. 4: In vivo prolyl endopeptidase (PEP)-supplemented digestion of P5 (A)—co-perfused with pepsin-, trypsin-, and chymotrypsin digested gliadin into a 20-cm segment of rat intestine in vivo.

To verify that PEP has adequate specificity so as to target P5 when present as a component of a mixture of gliadin peptides, the intestinal perfusion experiment was repeated by co-perfusing 41.7 μg/mL recombinant PEP (~190 μU/μL) and P5 along with 2 mg/mL gliadin that had been pretreated with pepsin, chymotrypsin, and trypsin. As seen in FIG. 4, P5 was efficiently eliminated by PEP, accumulation of the non-toxic peptide products (SEQ ID NO:20) PQPQP and (SEQ ID NO:26) QPQLPYP or (SEQ ID NO:23) QLPYPQP occurs as shown in FIG. 1. Thus, efficient cleavage of P5 was observed, even in the presence of a large number of smaller gliadin fragments that might compete for the PEP active sites.

Figure 5:
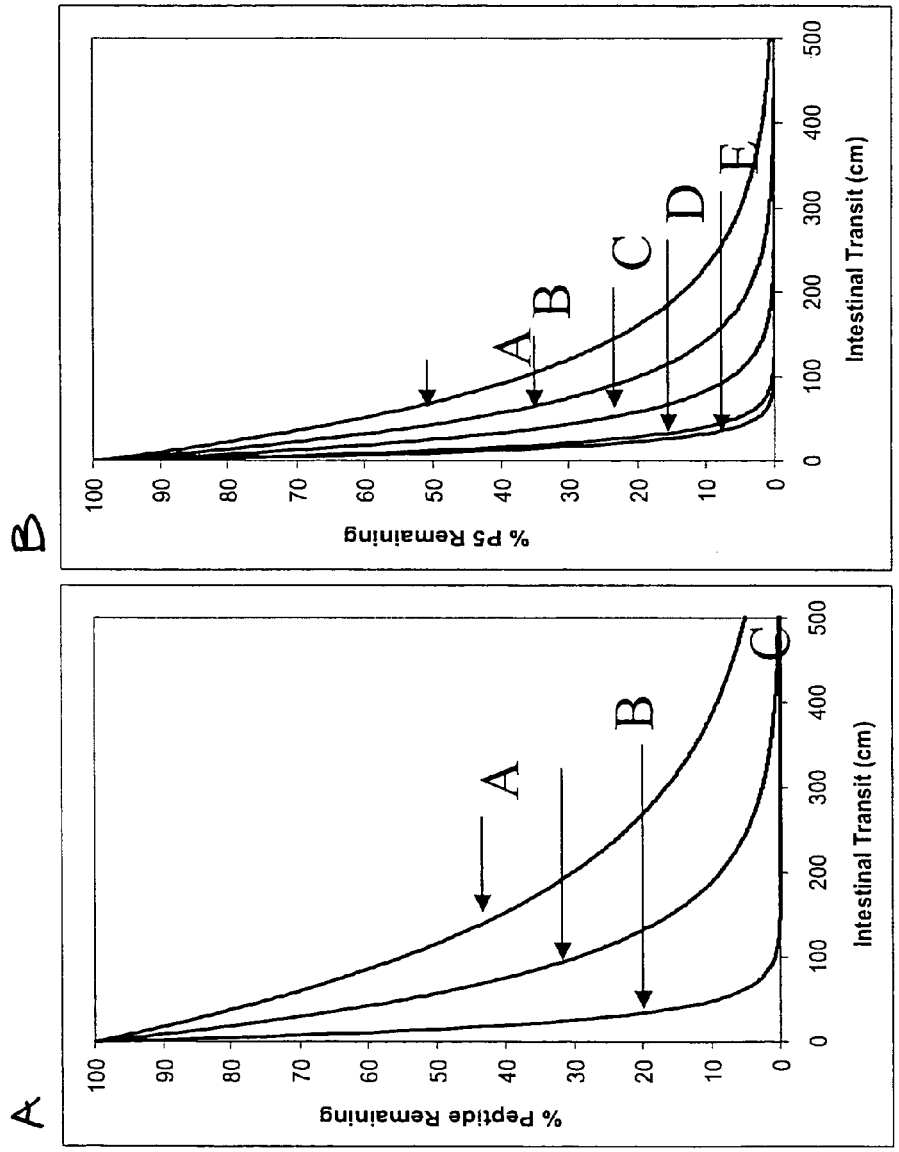
FIGS. 5A-5B: Calculated model for 100 µM P5 (A), 100 µM P4 (B), and 100 µM P10 (C) luminal intestinal digestion using in vivo rat intestinal perfusion results.

A Model for Intestinal Content of Toxic Gliadin Peptides. The intestinal content for P4 and P5 during intestinal transit was calculated using the in vivo data collected in this work (FIG. 5A). The model not only indicates the importance of intestinal digestion in these gastric and pancreatic resistant fragments, but also highlights the relative resistances to proteolysis by the brush border enzymes. The model predicts that the concentration for the control peptide myoglobin should be reduced to <1% starting material within 100 cm (the human upper small intestine). However, P4 persists >375cm (the human lower small intestine) and P5 declines only to ~5% after passing through the entire small intestine. In addition, data previously collected for P4 and P5 were used to determine the effect of transport across the epithelium on the concentration profile. The overall effect on the luminal content was minimal, altering the average retention times of P4 and P5 by <7%. On the other hand, co-perfusion of 41.7 μg/mL recombinant PEP (~190 μU/μL) with P5 effectively reducing the luminal content to <1% with 75 cm, an 8-fold reduction in average retention time (FIG. 5B).

The work presented here quantifies the relative proteolysis resistance of several gliadin peptide segments and quantifies the in vivo role of prolyl endopeptidase as a potential enzymatic supplement to digestion of these toxic gliadin peptides. The luminal content model for gliadin peptide proteolysis illustrates the relative resistance of these gliadin peptides and the hydrolytic effects of PEP on luminal peptide content.

Incubating the panel of α- and γ-gliadin derived peptide fragments with proteases that they are typically exposed to in the stomach and upper intestine (pepsin, trypsin, chymotrypsin, carboxypeptidase A, and elastase) revealed, with the exception of P6, that the peptides were almost completely resistant to proteolysis by these enzymes (≧90% remaining after 4 hours; Table 2). Certainly, there is a variable resistance of gliadin fragments to surface digestion and some of the gliadin peptides are highly resistant to BBM processing. Since P6 is readily digested, it is unlikely to accumulate in the intestine to have a toxic effect due to macrophage stimulation. The BBM was able to proteolyze some of the gliadin peptides, reducing them to ≦10% of the starting material, although this required 4 hours of exposure under physiologically relevant conditions (Table 2). In particular, both P5 and P8 remained at ~70% of the starting material even after 4 hours. These results indicate that the brush border enzymes are capable of cleaving many potentially toxic gliadin peptides to smaller non-toxic fragments, but at relatively slow rates that can be expected to allow the parent peptide to reside for an extended period within the upper intestinal cavity to evoke a toxic response in the Celiac Sprue. Notably, the BBM action on P5, the 33-mer known to be highly immunogenic by its capacity to stimulate T cell replication, is minimal (FIG. 1). Only the C-terminal Phe residue is removed, leaving the still toxic 32-mer peptide as the product.

The addition of PEP cleaves it further to 4- to 7-mers that are substrates for subsequent surface digestion by the BBM oligopeptidases. Whereas some peptides are degraded into easily assimilated fragments, relatively long intermediates accumulate in the lumen in other instances (FIG. 1). These two points demonstrate the possibility of two categories of digestive-resistant toxic peptides. The first category consists of highly resistant gliadin peptides such as P5 and P8; notably, P5 has already been shown to be a highly potent trigger of T cell proliferation from Celiac patients. The second category is composed of the less digestive-resistant, but still toxic, gliadin peptides that may be processed to non-toxic products in Celiac patients. Notably, the latter category of gliadin peptides may play a role only after the intestinal Celiac lesion has become well established with consequent reduction in brush border enzyme expression (Mercer et al., 1990), thereby allowing the less resistant gliadin peptides to persist in the intestinal lumen.

At a low dose of PEP (25 µU/µL), the processing rates of the gliadin peptides were enhanced by ~50% (FIG. 2), but not to the high levels of digestion seen for the control peptides. When PEP concentration were increased to 190 µU/µL, in the in vivo perfusion experiments, P5 (33-mer) could be shown to be completely cleaved to small non-toxic peptides (FIG. 3). These dosing levels (1:50 to 1:5; PEP to peptide) compare favorably to dosing levels currently in use for treating lactose intolerance (1:100 to 1:10; lactase to lactose) indicating that these dosing levels are in a reasonable range. Also, despite the possible competitive effect of other gliadin peptide fragments that would be released by pancreatic protease action on gluten within the intestinal lumen, perfusion of gluten pre-treated with pepsin and pancreatic proteases along with P5 did not interfere with the efficient processing of the peptide to its non-toxic products (FIG. 4).

Currently it is not known what quantities of intact peptide are required to initiate and maintain the Celiac inflammatory response. The compact non-gliadin peptide, GLGG, is efficiently digested, and comparison of proteolysis for the gliadin peptides to those for GLGG, P10, and P9, may provide insight concerning the elimination of toxic gliadin in the intestine. The in vivo rate data indicate that toxic gliadin peptide digestion is an order of magnitude slower than that for GLGG, and is reduced by >50% as compared to the digestion of the non-gliadin peptides. It has been suggested that PEP is capable of accelerating the proteolysis of resistant gliadin peptides. In the work presented here, PEP supplemented digestion of P5 and P8 showed significant increases in proteolysis rates in both in vitro and in vivo assays. PEP addition was capable of decreasing the in vitro concentrations of the majority of gliadin peptides tested to below 10% of those persisting after maximal gastric and pancreatic protease action.

Furthermore, in vivo PEP increases the rate of proteolysis by >50% (Table 2), additional PEP dosing indicates that luminal gliadin concentration of these peptides can be reduced or be potentially eliminated. Using the quantitative data collected here, profiles of the luminal content for P4 and P5 were calculated. These profiles clearly illustrate the proteolysis resistance of these gliadin peptides with the gliadin peptides persisting 4-8 times longer than a physiologically relevant peptide from myoglobin (FIG. 5A). The profile for luminal content was re-calculated using previously collected data for flux of P4 and P5 across the epithelium which determined a minimal effect on the luminal content. Further support for the beneficial effects of PEP supplementation is gained by analyzing the PEP dosing experiment presented in a similar manner (FIG. 5B). These results clearly illustrate the dramatic effect of PEP on luminal peptides. The work presented here has demonstrated the resistance of several immunogenic gliadin peptides to gastric, intestinal brush border proteolysis. Furthermore, we have determined that there appear to be two levels of resistance, one at the gastric and luminal (pancreatic) protease level, and one at the brush border peptidase level. The in vivo rate data have shown that the reduced rate of proteolysis is not solely due to size, and that PEP can function in concert with the brush border peptidases by providing the initial key cleavages on a number of peptides so as to increase the overall rate of peptide processing.

Dosing experiments have also confirmed that highly resistant peptides such as P5 can effectively be eliminated with PEP supplemented digestion with minimal accumulation of products. Perfusion of pepsin-, trypsin-, and chymotrypsin-digested gliadin with P5 has demonstrated that PEP is capable of digesting P5 even in the presence of smaller, more accessible targets which would be present under physiological conditions (FIG. 4). Digestion of P5 under these conditions is at least comparable to that for the other gliadin digestive resistant fragments released after completed processing of gluten by pepsin, trypsin, and chymotrypsin, further suggesting that PEP has appreciable potential as a digestive supplement. Luminal profiles of gliadin content illustrate the relative proteolysis resistance of these gliadin peptides compared to physiologically relevant myoglobin peptide and that flux across epithelial cells only plays a minor role in determining luminal gliadin content (FIG. 5A). Furthermore, the abundance of toxic peptides calculated from the PEP dosing experiments establishes a dramatic effect of PEP on luminal concentration with a 3-fold increase in rate resulting in an 8-fold reduction in average retention time (FIG. 5B).

It is important to continue whole gliadin proteolysis studies, to determine other potentially resistant fragments. This should allow the identification, quantification, and the stimulatory capacity of PEP-resistant peptides to be defined. Given the importance of understanding the digestion of these gliadin peptides and of determining the means to detoxify these peptides, it is important to elucidate the in vivo situation of a complex organ such as the intestine. Using the rat intestinal perfusion set-up as our model system of digestion, we hope to further study PEP as a potential detoxifying agent and try to understand key events in the digestion and uptake of these gliadin peptides in order to prevent the cascade of events that follows in Celiac Sprue.

EXAMPLE 2

Peptidase Supplementation as Therapy for Celiac Sprue—Demonstration of Efficacy and Safety in Rats and Humans In Vivo Once the ideal ratio of PEP to gliadin peptide is determined in these perfusion experiments, one can analyze the capacity of the PEP to enhance the hydrolysis of gluten peptides in commercial gluten-containing wheat flour. A 1% slurry of the flour mixed with 1:100 (weight basis) trypsin and chymotrypsin, and 1:500 (weight basis) elastase is perfused into the intestine with or without co-perfusion of suitable. quantities of the PEP. LC-MS analysis of the residual gliadin products is conducted on the collected samples, and the histologic and enzymatic parameters are examined, as described above.

Feeding studies in intact rats can be conducted as follows. Once the ideal ratio of the PEP to the gliadin substrate has been established in the perfusion experiments, rats are fed 70% carbohydrate chow containing wheat flour, which is used as the conventional rat chow for periods of two weeks. Control rats are fed only the special chow, and the treated rats are given sufficient PEP supplementation (molar ratios PEP to gliadin protein: 1:1, 1:10 and 1:100) in the diet to digest the residual gliadin peptides such as the Pro- and Gln-rich 33-mer. After two weeks of ab lib feeding, the rats' daily consumption of food is quantified by daily weighing of the residual chow in the feeder and the nutritional assessment determined by daily body weights. Over the feeding period of 2-4 weeks, rats are weighed and examined daily to verify normal activities and are then killed by stunning and decapitation. The intestine, liver and kidneys are recovered and examined for gross and histological integrity, and any anatomic differences are noted between the control (PEP−) and treated (PEP+) animals. In addition, digestive enzymes (carbohydrases and proteases) are determined, as detailed for the rat perfusion studies.

Preliminary clinical testing of the efficacy of PEP in processing the resistant gliadin peptides can be conducted as follows. Now that it has been established that PEP can readily convert the high-Pro, high-Gln gliadin peptides to smaller, non-toxic fragments that do not produce proliferation in the T cell assay, preliminary testing of PEP treated wheat flour containing the usual or enhanced amounts of gluten (e.g., Bob's RedMill flour, Milwaukee, Oreg.) or food-grade gluten or gliadin itself (e.g. gliadin from Sigma Aldrich) can be undertaken. The flour, gluten or gliadin can be batch treated with appropriate amounts of purified mixtures of pancreatic enzymes that are used clinically to treat pancreatic insufficiency (e.g., Pancrease MT 20 containing 20,000 units lipase, 44000 units of the pancreatic proteases and 56000 units of amylase per capsule). Incubation of a slurry of flour, gluten or gliadin with the material from an appropriate amount of capsules of the Pancrease preparation can be carried out in 0.02 M Na-K phosphate buffer, pH 6.5 at 37° C. for several hours under sterile conditions until 1) standard T cell proliferation assays (see, for example, Arentz-Hansen, 2000) identifies the highly active signal produced by the gliadin peptides and particularly 33-mer, ((SEQ ID NO:12) LQLQPF-PQPQLPYPQPQLPYPQPQLPYPQPQPF) and 2) the average size of the proteolytically derived gliadin peptides has been reduced to <6 residues (as measured by gel filtration HPLC). The pre-digested flour, gluten or gliadin is then exposed to sufficient pure PEP (for example, 1 mole PEP:100 moles gliadin substrate) under sterile conditons for 1-18 hours, and the cleavage of gliadin peptides with known toxicity such as the 33-mer verified by LC-MS analysis. In parallel control studies, previously denatured PEP (by heating to 90° C. for 60 min) can be incubated with the protease-treated flour and the persistence of these toxic peptides is verified by LC-MS analysis. These tests demonstrate the usefulness of a the 33-mer in assays; in one aspect, the present invention provides the 33-mer in isolated and purified forms, as well as assays to detect its present in foodstuffs.

The pre-treated flours can be incorporated into otherwise gluten-free breakfast muffins by a nutritionist, and these served to volunteer persons and those with biopsy-proven Celiac Sprue at a "community" breakfast in the nutrition department for a period of two weeks. Patients must have uncomplicated Celiac Sprue that is in remission on gluten exclusion alone. Control volunteers who have been established not to have Celiac Sprue and negative Celiac antibody studies are also recruited. During this period the control muffins made with flour that has been treated with denatured pancreatic proteases±PEP are given. The PEP+ muffins are given for the first two weeks followed by a two week break from the breakfasts, and the PEP− muffins are administered over the second two week breakfast sessions. The study can be single-blinded, the subjects being unaware of whether PEP is included in the study. The physician and nutritionist will know the flour has been exposed only to the pancreatic proteases or also to PEP, in case there are any untoward reactions to the PEP material. All study subjects will fill out a questionnaire regarding their observations during each two week period as well as during the two week break time and the two weeks after the second muffin breakfast period. Although obtaining a biopsy via endoscopy would be an ideal monitor of the PEP efficacy, this cannot be ethically justified based on currently available data. Endoscopy may be offered only if needed as an aspect of patient care. Participants will initially meet briefly with the responsible physician-investigator who will be available throughout the study. Participants will be interviewed and the questionnaire reviewed by a nutritionist and physician before the study, at the end of each two week period and two weeks after completing the study. The principal investigator will be ultimately responsible for the conduct of the trial and will meet regularly with the responsible physician and nutritionist to whom the day to day aspects of the study will be delegated. Adults from age 17 and older can be eligible for the study. Both males and females with Celiac Sprue will be recruited through Celiac support organizations. Individuals from various ethnic groups, including Asian and African American can be recruited, although most patients with Celiac Sprue are Caucasians. Both males and females can participate; there is a somewhat higher proportion of female Celiac Sprue patients (~65%). Participants will have 24 hour access to the gastroenterology team, and a member of the research team will be available for consultation. Efficacy will be monitored by the comparative responses of participants during the control period when ingesting protease-treated flour without the PEP versus the same flour that has been treated with PEP.

Suitable conditions for packaging the rPEP to achieve efficient digestion of gliadin peptides in vivo can be determined as follows. To develop a palatable preparation of PEP to enable the in vivo digestion of the toxic peptides in humans, it can be useful to formulate PEP so that it can pass into the small intestine without being destroyed by the harsh acidic environment of the stomach. In addition, this formulation can provide rapid release of PEP upon entry into the duodenum, where the secreted pancreatic proteases exert their maximal action within the luminal contents to cleave dietary proteins. There are several well-studied and widely used examples of such delivery systems for other substances. The development of an optimized formulation for an effective PEP drug capable of delivering pharmacologically useful quantities of this enzyme into the upper small intestine as a digestive supplement can be conducted as follows. To process the digestive-resistant gliadin peptides, selected formulation strategies that have been used successfully for the delivery of other enzyme supplements can be used. In particular, previously used formulations for pancreatic proteases and lactase are evaluated by use of recombinant PEP from *Flavobacterium meningosepticum* and *Aeromonas hydrophila*. These enzymes are expressed and purified as described by A. Kitazono et al. and A. Kanatani et al. Pancreatic enzymes have been used for the past seventy years to treat pancreatic exocrine insufficiency. Although early clinical results were variable due to gastric inactivation of the exogenously administered enzymes, a revived interest in enzyme-containing digestive aids occurred around 1960 with the development of acid stable enteric coatings (I. R. Wilding, S. S. Davis, and D. T. O'Hagan, Targeting of drugs and vaccines to the gut. *Pharmac. Ther.* 62, 97-124, (1994)). Similarly, acid stable enteric coatings have also been used for the delivery of lactase into the duodenum of patients with lactase deficiency. In one embodiment, the glutenase formulations of the invention comprise a glutenase in a stable enteric coating.

Lyophilized, particulate PEP mixed with bicarbonate (as buffer) is coated with Eudragit S100, L30D or L 100-44 according to manufacturer's instructions (Rohm America). Alternatively, cellulose acetate phthalate, methylcellulose or hydroxypropylmethyl cellulose phthalate can be used as coatings for the preparation of gastric acid resistant pellets. These enteric coatings are commonly used for the formulation of pancreatin (see T. Sipos (1978), Preparation of enteric coated digestive enzyme compositions, U.S. Pat. No. 4,079,125; and T. Sipos (1998), High buffer-containing enteric coating digestive enzyme. bile acid compositions and method of treating digestive disorders therewith, U.S. Pat. No. 5,750, 104).

An alternative strategy useful in preparing formulations of the invention, used successfully with lactase (B. J. Langner (1999), Enteric polymer coated capsule containing dried bacterial culture for supplying lactase, U.S. Pat. No. 6,008,027), involves filling gelatin capsules with 50-90% lyophilized PEP, the remaining capacity being filled with stabilizing dessicants such as silicon oxide, silicon dioxide or microcrystalline cellulose and bicarbonate buffer. The capsules are enterically coated with Eudragit polymer (Rohm America) or polyvinyl acetate phthalate (Sureteric, Merck Frosst) and vacuum dried prior to use. Similarly, diastase has been formulated with Eudragits RS100 and cellulase acetate phthalate coatings for enteric use (S. P. Vyas, P. J. Gogoi, S. Pande, and V. K. Dixit, Enteric spherules diastase in enzyme preparations. *J. Microencapsulation.* 8, 447-454, 1991). To demonstrate that these or other formulations increase PEP bioavailability in the small intestine, one can perform the following experiments. First, the ability of PEP activity to withstand 0.5-2 h of simulated gastric treatment (pepsin, in 0.1N HCl, pH 2) can be evaluated. If >10% activity can be reproducibly retained, the formulation is exposed to simulated conditions in the duodenum (pH 6.5 buffer containing trypsin, chymotrypsin and carboxypeptidase at a 1:100 molar ratio and elastase at a 1:500 ratio to the putative α2-gliadin). Ideally, full release of PEP activity would be achieved within 15 minutes. Formulations that satisfy the above criteria are fed initially to adult rats in conjunction with gluten-free meals spiked with recombinant α2-gliadin (whose proteolytic behavior in response to gastric and pancreatic enzymes+PEP has been well characterized). PEP doses in the range of 10-1000 units/kg body weight can be evaluated. Animals are sacrificed two hours after meals, and the small intestinal derived contents are analyzed by LC-MS for residual PEP activity and the extent to which gliadin has been proteolyzed. In particular, the concentration of the 33-mer digestive-resistant gliadin peptide is estimated. Formulations that yield >90% reduction in concentration of this peptide are evaluated more extensively for potential toxicity, as detailed above for the initial rat studies with water soluble PEP.

The procedures described herein are performed under an approved Animal Protocol described below. Male Sprague-Dawley rats, 250-300 g, (or Fisher rats for studies of DPP IV deficient intestine) are allowed access to regular wheat-based rat chow until the experiment. Rats are allowed water only for 8 hours prior to the experiment to insure clearance of residual chow in the upper small intestine. After the rat is anesthetized with an intraperitoneal injection of pentobarbital (50 mg/Kg), the abdominal cavity is opened and a small incision made in a segment of jejunum located 10 cm beyond the ligament of Trietz. Cannulation is made with a polyethylene catheter (3 mm ID, 4 mm OD) and sutured 2 cm distal to the incision. A second cannula is placed in similar fashion 10 cm distal to the first with the cannula facing proximally. After rinsing the isolated, intact jejunal segment with Ringer's solution (140 mM NaCl, 10 mM KHCO$_3$, 1.2 mM K$_2$HPO$_4$, 1.2 mM CaCl$_2$, 1.2 mM MgCl$_2$) at 37° C. to remove any intraluminal debris, the isolated loop of intestine is returned to the abdominal cavity. The incision is covered with clear plastic wrap, and intra-abdominal temperature maintained at 37° C. by positioning a 30 watt incandescent lap at ~30 cm from the animal. A 2 mM solution of a gliadin peptide of 7-14 residues (purified and characterized by HPLC-Mass Spectrometry) is perfused in Ringer's solution containing [$^{14}$C]inulin (a dilution-concentration marker) to establish a steady state of concentrations of residual peptide and smaller products at the collection distal collection site (previous studies with other peptides and carbohydrates have revealed the steady state to be achieved in 10-20 minutes). Samples collected at the distal site are recovered and analyzed by HPLC-MS for residual peptide and smaller peptide or amino acid products. Samples are collected over 3 successive 10 minute periods after a steady state is achieved, and a series of gliadin and non-gliadin peptides are used. Animals can usually be maintained under anesthesia for a period of 3 to 6 hours by the addition of small increments of pentobarbital (~5 mg per 30-60 minutes). At the end of the experiment, the intestinal segment and an adjacent control segment are recovered and samples taken from liver, kidney and blood for analysis of the test peptide and its products. Terminal euthanasia is accomplished by an overdose of anesthesia to produce apnea until there is no heart contraction.

While other methods and reagents can be employed for purposes of the present invention, this example provides enzymes, enzyme formulations, and animal and clinical testing protocols to demonstrate the efficacy of enzyme-mediated therapy for Celiac Sprue.

EXAMPLE 3

Heterologous Expression of PEP in *Lactobacilli*

In one embodiment of the present invention, a Celiac Sprue patient is provided with a recombinant organism modified to express a PEP of the invention. The recombinant organism is selected from those organisms that can colonize the intestinal mucosa without detriment to the patient, thereby providing an endogenous source of PEP to the patient. As one example, *Lactobacilli* such as *L. casei* and *L. plantarium* can colonize the intestinal mucosa and secrete PEP enzymes locally. Given their widespread use in food processing, they can also be used as an efficient source of PEP for industrial (to treat foodstuffs) and medical (to prepare PEP for pharmaceutical formulation) use. PEPs can be expressed in such *lactobacilli* using standard recombinant DNA technologies. For example, Shaw et al. (Shaw, D M, Gaerthe, B; Leer, R J, Van der Stap, J G M M, Smittenaar, C.; Den Bak-Glashouwer, Heijne, M J, Thole, J E R, Tielen F J, Pouwels, P H, Havenith, C E G (2000) Immunology 100, 510-518) have engineered *Lactobacilli* species to express intracellular and surface-bound tetanus toxin. The intact PEP genes (including leader sequences for efficient bacterial secretion) can be cloned into shuttle expression vectors such as pLP401 or pLP503 under control of the (regulatable) amylase promoter or (constitutive) lactate dehydrogenase promoter, respectively. Alternatively, recombinant food grade *Lactobacilli* strains can be generated by site specific recombination technology (e.g. see. Martin M C, Alonso, J C, Suarez J E, and Alvarez M A Appl. Env. Microbiol. 66, 2599-2604, 2000). Standard cultivation conditions are used for *Lactobacilli* fermentation, such as those described by Martin et al.

EXAMPLE 4

Heterologous Expression of PEP in Yeasts

Both naturally occurring and recombinant cells and organisms can be used to produce the glutenases useful in practice of the present invention. Preferred glutenases and producing cells include those from organisms known to be Generally Regarded as Safe, such as *Flavobacterium, Aeromonas, Sphingomonas, Lactobacillus, Aspergillus, Xanthomonas, Pyrococcus, Bacillus* and *Streptomyces*. Extracellular glutenase enzymes may be obtained from microorganisms such as *Aspergillus* oryzae and *Lactobacillus casei*. Preferred cells include those that are already used in the preparation of foodstuffs but have been modified to express a glutenase useful in the practice of the present invention. As one example, yeast strains such as *Saccharomyces cerevisiae* are useful for high level expression of secreted heterologous proteins. Genes encoding any of the PEPs described above (mature protein only) can be cloned in expression plasmids designed for optimal production of secreted proteins. An example of such a heterologous expression strategy is described in Parekh, R. N. and Wittrup, K. D. (Biotechnol. Prog. 13, 117-122, 1997). Either self-replicating (e.g. 2 micron) or integrating (e.g. pAUR101) vectors can be used. The GAL1-10 promoter is an example of an inducible promoter, whereas the ADH2 promoter is an example of a constitutive promoter. The cDNA encoding the mature PEP is fused downstream of a leader sequence containing a synthetic pre-pro region that includes a signal cleavage site and a Kex2p cleavage site. *S. cerevisiae* BJ5464 can be used as a host for production of the peptidase. Shake-flask fermentation conditions are described by Parekh and Wittrup in the above-cited reference. Alternatively, high cell density fed-batch cultures can be used for large scale production of the peptidases; a representative procedure for this purpose is described in Calado, C. R. C, Mannesse, M., Egmond, M., Cabral, J. M. S. and Fonseca, L. P. (Biotechnol. Bioeng. 78, 692-698, 2002).

EXAMPLE 6

Enteric Capsule Formulation of Prolyl Endopeptidase

Gelatin capsules are filled with 100 mg prolyl endopeptidase and 10 mg of silicon dioxide. The capsules are enterically coated with Eudragit polymer and put in a vacuum chamber for 72 hours. The capsules are then held at a range of temperature of 10° C. to 37° C. and a controlled humidity level of 35-40%.

EXAMPLE 6

Studies of Enteric Capsule Formulation of Prolyl Endopeptidase

A study is conducted where patients with Celiac Sprue are enrolled in a two week-long study. Gelatin capsules containing 90% prolyl endopeptidase mixed with 10% silicon dioxide are used. The capsules are hand-filled with the mixture, banded, and coated with a 10% Sureteric enteric coating (a polymer of polyvinylacetatephthalate developed by the Canadian subsidiary of Merck & Company). Samples are acid-tested by exposing the coating to 1 N HCL for one hour in order to simulate the acid environment of the stomach. The capsules are then put in a vacuum chamber for 72 hours.

Two 100 mg capsules are administered to each patient prior to each meal. The patients are instructed to eat all kinds of food without abstaining from those that were known to cause distress, e.g., bloating, diarrhea, and cramps.

EXAMPLE 7

Enteric Pill Formulation of Prolyl Endopeptidase 400 mg of L-tartaric acid and 40 mg of polyethylene glycol-hydrogenated castor oil (HCO-60) are dissolved in 5 ml of methanol. This solution is placed in a mortar previously warmed to 30° C. To the solution is added 100 mg of prolyl endopeptidase. Immediately after the addition of PEP, the mixture is stirred with a pestle under a hot air current (40° C.) and then placed in a desiccator under vacuum overnight to remove the solvent. The resulting solid-mass is pulverized with a pestle and kneaded with 30 mg of sodium bicarbonate and a small amount of 70% ethanol. The mixture is then divided and shaped into pills of about 2 mm size and thoroughly dried. The dried pills are given a coating of hydroxypropylmethylcellulose phthalate (HP-55) to obtain an enteric formulation.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. A method of determining the therapeutic efficacy of a candidate glutenase enzyme, the method comprising:
   detecting the ability of a candidate enzyme to digest one or more peptides selected from the group consisting of (SEQ ID NO:4) FLQPQQPFPQQPQQPYPQQPQQPFPQ; (SEQ ID NO:5) IQPQQPAQL; (SEQ ID NO:27) QQPQQPYPQ; and (SEQ ID NO:28) SPQQQFPQ to fragments that are non-toxic to Celiac sprue patients.

2. The method according to claim 1, further comprising the step of detecting the ability of a candidate enzyme to digest the peptide (SEQ ID NO:12) LQLQPFPQPQLPYPQPQLPYPQPQLPYPQ PQPF.

3. The method of claim 1, further comprising performing an HPLC-trace to determine the products of digestion.

4. The method according to claim 1, wherein the detecting step comprises mixing said one or more peptides with said candidate enzyme in a reaction mixture and perfusing into an intact intestine in an animal model.

5. The method of claim 4, further comprising performing an HPLC trace to determine the products of digestion.

6. The method of claim 1, wherein the detecting step comprises mixing said one or more peptides with said candidate enzyme in a reaction mixture comprising one or more intestinal brush border enzymes.

7. The method of claim 1, wherein the detecting step comprises mixing said candidate enzyme in a reaction mixture comprising the peptides, wherein the peptides have been pre-treated with pepsin under physiological conditions.

8. The method of claim 1, wherein the detecting step comprises mixing said candidate enzyme in a reaction mixture comprising the peptides, wherein the peptides have been pre-treated with trypsin, chymotrypsin, elastase, and carboxypeptidase.

9. The method of claim 7, wherein said peptides, prior to said mixing step, are further pre-treated with trypsin, chymotrypsin, elastase and carboxypeptidase.

10. The method of claim 1, wherein the peptide is (SEQ ID NO:4) FLQPQQPFPQQPQQPYPQQPQQPFPQ.

11. The method of claim 1, wherein the peptide is (SEQ ID NO:5) IQPQQPAQL.

12. The method of claim 1, wherein the peptide is (SEQ ID NO:27) QQPQQPYPQ.

13. The method of claim 1, wherein the peptide is (SEQ ID NO:28) SPQQQFPQ.

* * * * *